US012694982B2

(12) United States Patent
Gates et al.

(10) Patent No.: US 12,694,982 B2
(45) Date of Patent: *Jul. 28, 2026

(54) DETERMINATION OF HEALTH SCIENCES RECOMMENDATIONS BASED ON MULTIDIMENSIONAL NONLINEAR MANIFOLD CLUSTERING

(71) Applicant: Edge2020 LLC, Herndon, VA (US)

(72) Inventors: Tell Gates, Great Falls, VA (US); Ronald Hirsch, Herndon, VA (US)

(73) Assignee: EDGE2020 LLC, Herndon, VA (US)

( * ) Notice: Subject to any disclaimer, the term of this patent is extended or adjusted under 35 U.S.C. 154(b) by 1001 days.

This patent is subject to a terminal disclaimer.

(21) Appl. No.: 17/834,770

(22) Filed: Jun. 7, 2022

(65) Prior Publication Data

US 2022/0375611 A1 Nov. 24, 2022

Related U.S. Application Data

(63) Continuation of application No. 16/142,905, filed on Sep. 26, 2018, now Pat. No. 11,355,240.

(Continued)

(51) Int. Cl.
| | |
|---|---|
| *G16H 50/00* | (2018.01) |
| *G06F 21/62* | (2013.01) |

(Continued)

(52) U.S. Cl.
CPC ......... *G16H 50/20* (2018.01); *G06F 21/6245* (2013.01); *G06N 3/042* (2023.01); *G06N 3/088* (2013.01); *G16H 20/10* (2018.01);

*G16H 20/40* (2018.01); *G16H 20/70* (2018.01); *G16H 50/70* (2018.01); *G16H 70/00* (2018.01);

(Continued)

(58) Field of Classification Search
None
See application file for complete search history.

(56) References Cited

U.S. PATENT DOCUMENTS

| | | | |
|---|---|---|---|
| 8,073,528 B2 * | 12/2011 | Zhao | G16H 40/67 |
| | | | 700/245 |
| 8,792,963 B2 * | 7/2014 | Zhao | A61B 34/20 |
| | | | 382/128 |

(Continued)

*Primary Examiner* — Farhan M Syed
(74) *Attorney, Agent, or Firm* — Hickman Becker Bingham Ledesma LLP; Matthew Loppnow

(57) ABSTRACT

A method and apparatus can include a system controller and a system processor. The system controller can retrieve a health science related dataset from at least one database, the retrieved dataset including information associated with at least one of a patient medical information, healthcare provider clinical information, health related publications and treatment information, and pharmaceutical information, and transmit to a user equipment a recommendation of at least one of health diagnosis and treatment for a patient. The system processor can utilize multidimensional nonlinear manifold clustering on at least one element from the retrieved dataset, assign an entity formulated from the at least one element of the retrieved dataset into a decision hyper-volume based on the multidimensional nonlinear manifold clustering, and determine the recommendation of at least one of health diagnosis and treatment for the patient based on the assignment of the entity into the decision hyper-volume.

38 Claims, 4 Drawing Sheets

Related U.S. Application Data

(60) Provisional application No. 62/563,448, filed on Sep. 26, 2017.

(51) Int. Cl.

| | |
|---|---|
| *G06N 3/042* | (2023.01) |
| *G06N 3/088* | (2023.01) |
| *G16H 20/10* | (2018.01) |
| *G16H 20/40* | (2018.01) |
| *G16H 20/70* | (2018.01) |
| *G16H 50/20* | (2018.01) |
| *G16H 50/70* | (2018.01) |
| *G16H 70/00* | (2018.01) |
| *H04L 9/40* | (2022.01) |

(52) U.S. Cl.

CPC ...... *H04L 63/0407* (2013.01); *H04L 63/1433* (2013.01); *H04L 63/1441* (2013.01); *H04L 63/0428* (2013.01)

(56) References Cited

U.S. PATENT DOCUMENTS

| | | | | |
|---|---|---|---|---|
| 11,145,390 | B2 * | 10/2021 | Will | G16H 50/70 |
| 2009/0088634 | A1 * | 4/2009 | Zhao | A61B 1/00193 |
| | | | | 600/425 |
| 2009/0131758 | A1 * | 5/2009 | Heywood | G16H 40/20 |
| | | | | 600/300 |
| 2012/0020547 | A1 * | 1/2012 | Zhao | G16H 30/40 |
| | | | | 382/153 |
| 2014/0279746 | A1 * | 9/2014 | De Bruin | G16H 50/70 |
| | | | | 706/46 |
| 2017/0206327 | A1 * | 7/2017 | Heywood | A61B 5/4833 |
| 2018/0342323 | A1 * | 11/2018 | Shankar | G16H 50/20 |
| 2019/0082990 | A1 * | 3/2019 | Poltorak | A61B 5/372 |
| 2019/0087727 | A1 * | 3/2019 | Skellenger | G16H 10/60 |
| 2019/0201691 | A1 * | 7/2019 | Poltorak | A61B 5/374 |
| 2019/0247662 | A1 * | 8/2019 | Poltroak | A61N 1/36092 |
| 2020/0027539 | A1 * | 1/2020 | Xie | G06F 18/211 |
| 2022/0020463 | A1 * | 1/2022 | Chen | G16H 50/20 |
| 2022/0059221 | A1 * | 2/2022 | Zhu | G06V 10/806 |

* cited by examiner

DETERMINATION OF HEALTH SCIENCES RECOMMENDATIONS BASED ON MULTIDIMENSIONAL NONLINEAR MANIFOLD CLUSTERING

This application claims priority to U.S. patent application Ser. No. 16/142,905, entitled "DETERMINATION OF HEALTH SCIENCES RECOMMENDATIONS", filed on Sep. 26, 2018, to Gates et al., which claims priority to U.S. Provisional Application No. 62/563,448, entitled "CLUSTERING AND ADJUDICATION TO DETERMINE DECISIONS FOR MULTIPLE APPLICATIONS", filed on Sep. 26, 2017, to Hirsch et al., the entirety of which is expressly incorporated herein by reference.

BACKGROUND

1. Field

Applicant's disclosed features provide such a real-world technical benefit to a real-world technical deficiency within the art of health sciences. More particularly, the present disclosure is directed to an apparatus and method for determining recommendations for health sciences diagnosis and/or treatment for a patient.

2. Introduction

Health sciences are evolving to meet new challenges. Challenges can include precision medicine (can also be referred to as personalized medicine), pandemics, antibiotic-resistant bacteria, new diseases, reemergence of old diseases, mutations of existing diseases, genetic disease, etc. These challenges require new methods and treatments that can (1) more rapidly diagnose new/existing/and/or mutated diseases, (2) discover new, existing, and/or repurposed drugs (or medicinal compounds) or a combination of these to fight disease or conditions, 3) discover interactions between drugs, food, environment, and genetic make-up that can cause diseases or other conditions, (4) new diagnostic procedures and/or symptoms and (5) an understanding of the genetic diseases and/or treatments (including deoxyribonucleic acid (DNA), ribonucleic acid (RNA), gene-editing (e.g., CRISPR (permanent changes to cell DNA), non-permanent changes to cell DNA, etc.), mutations and/or aging of DNA/RNA, proteins and other building blocks.

The key to understanding challenges and developing effective solutions/treatments can be contained in life-science data and determining missing and/or irrelevant data for a particular diagnosis and/or treatment. The method and apparatus presented in this application makes uses of a novel approach to machine learning (and/or deep learning) to determine the required and important data for each individual. Throughout this document individual and patient are used interchangeably. Also, a physician, hospital and/or other medical professionals can be referred to as a healthcare provider.

Machine learning and deep learning can reduce the burden and cost of Electronic Medical Records (EMR), advance the use of immunotherapy for cancer treatment, create reliable health risk predictors, create powerful diagnostic tools, create clinical decision support tools, create treatments, advance precision medicine, provide an experimental platform for medical/pharmaceutical/biological research, etc.

The advanced analytics performed by a disclosed Health Science Decision Support System (HSDSS) includes improvements to existing techniques and algorithms including, but not limited to, nonlinear manifold (NLM) clustering, Statistical Decision Theory, Neural Networks and/or a combination of these to control the HSDSS processing and data flow and optimize the results obtained. The approach presented herein use methods that can be optimized for detection, characterization, and exploitation of obscure structures, patterns and information in the data and/or metadata. Furthermore, this approach can discover confluence among relationships, processes and/or events, which can be useful in making health science recommendations.

BRIEF DESCRIPTION OF THE DRAWINGS

In order to describe the manner in which advantages and features of the disclosure can be obtained, a description of the disclosure is rendered by reference to specific embodiments thereof which are illustrated in the appended drawings. These drawings depict only example embodiments of the disclosure and are not therefore to be considered to be limiting of its scope.

DETAILED DESCRIPTION

The computer-based methods, systems and apparatuses disclosed herein can provide for recommendation making as applied to health science applications. The computer-based methods, systems and apparatuses disclosed herein can also provide for selection of cost-effective and resource-efficient recommendations for health sciences. Recommendation, discovery, detection, and identification are used interchangeably herein. Health sciences professionals can use these health science recommendations as a basis for making health science diagnosis and/or treatments for a patient.

Figure 1:
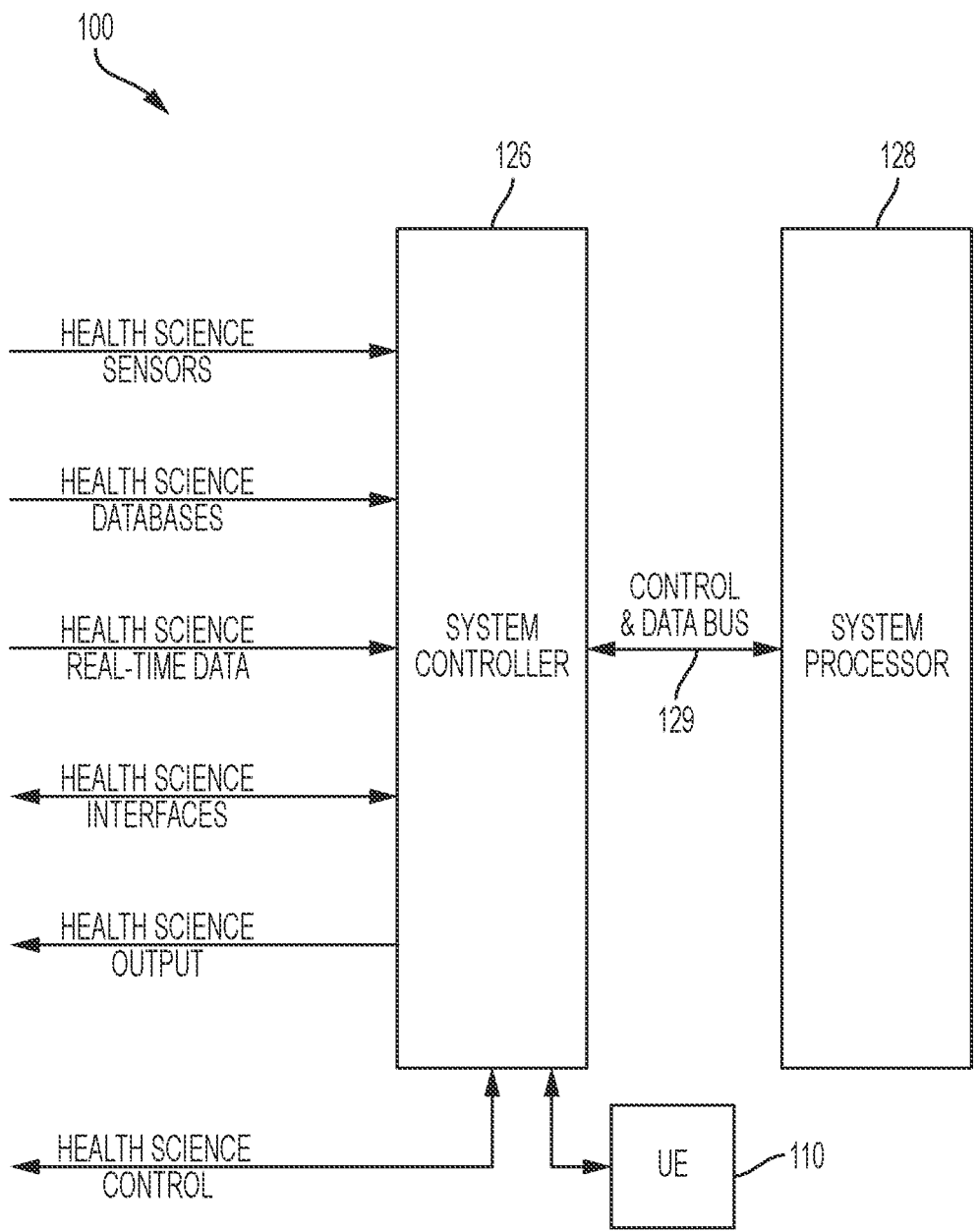
FIG. 1 illustrates an example of a Health Science Decision Processor (HSDP), in accordance with one or more possible embodiments.

FIG. 1 illustrates an example of the HSDP 100, in accordance with one or more possible embodiments. In particular, a system controller 126 can be coupled to a system processor 128. The system controller 126 can provide and/or retrieve selected data (including input, output and metadata and/or information) to and/or from the system processor 128. The system controller 126 can access and input application sensor metadata, databases, real-time data, interfaces into the system processor 128. Application control by the system user (including domain expert) can be done through the system controller 126. Application recommendations, actions, adjudication, and reasoning from the system processor 128 can be transferred to a user interface on a user device (not shown) via the system controller 126. The HSDP 100 can operate under the control of the multi-level, hierarchical adjudication, shown in more detail in FIG. 2.

For example, and as discussed in further detail herein, the system controller 126 can retrieve a health science related dataset from at least one database, the retrieved health science related dataset (hereafter referenced as retrieved dataset) including information associated with at least one of a patient medical information, healthcare provider clinical information, health related publications and treatment information, and pharmaceutical information. The system controller 126 can further transmit to the user equipment (UE) 110, such as a personal computer (PC), a tablet computer, a smart phone, augmented reality interface, or any other digital device that can receive and display digital information, and a recommendation of at least one of health diagnosis and treatment for a patient, including the Health Science Outputs (e.g. Table 9). The UE 110 can also provide control and feedback from input devices, such as a keyboard, mouse, eye and hand movement sensors, etc.

For example, and as discussed in further detail herein, the system processor 128 can perform various processes as a basis for determining the recommendation of at least one of health diagnosis and treatment for the patient. The system processor 128 can utilize multidimensional nonlinear manifold clustering on at least one element of the retrieved dataset, can assign an entity formulated from the at least one element of the retrieved dataset into a decision hyper-volume based on the multidimensional nonlinear manifold clustering, and can determine the recommendation of at least one of health diagnosis and treatment for the patient based on the assignment of the entity into the decision hyper-volume. In an example, the system processor 128 can formulate a health science related entity (hereafter referenced as an entity) from the retrieved dataset. In an example, the system processor 128 can divide the entity into two or more sub-entities.

For example, and as discussed further herein, the system processor 128 can perform adjudication to minimize a loss function in order to optimize the assignment of the entity by adjusting a decision boundary of the decision hyper-volume for the multidimensional nonlinear manifold clustering and at least one other type of multidimensional clustering including at least one of linear clustering, linear manifold clustering, and nonlinear clustering. In an example, the system processor 128 can perform adjudication to also select at least one of the multidimensional nonlinear manifold clustering and the at least one other type of multidimensional clustering based on a minimum loss function and optimum entity assignment. The system processor 128 can utilize a neural network to define the decision hyper-volume. In another example, the system processor 128 can perform adjudication to control a number of iterations of the selection of the retrieved dataset and/or entity and compare multiple iterations of the multidimensional nonlinear manifold clustering and at least one other type of multidimensional clustering. The system processor can apply the assignment of the entity regionally to an adjacent decision hyper-volume sharing a decision boundary. The system processor 128 can formulate a confidence region to rank an order of a plurality of the recommendation of at least one of health diagnosis and treatment. The system processor 128 can assign a recommendation to the decision hyper-volume based on at least one of supervised training and unsupervised training. The system processor 128 can perform adjudication to generate the entity to optimize the recommendation of diagnosis and/or treatment, that is to generate the best possible recommendation, as well as other possible recommendations that can be ranked ordered, of at least one of health diagnosis and treatment for a particular patient based on their particular associated traits or properties, examples of such particular traits or properties described herein.

In particular, the system processor 128 can accept data from the system controller 126, organize selected working data and transfers the output to one or more table(s) and the recommendation/action/reasoning results to the system controller 126. The system processor 128 can accept as input data from one or more databases, the one or more databases made up of a variety of elements such as shown in Tables 1 through 9. All input data can be received from the system controller 126. The system processor 128 can output results to the system controller 126. The system processor 128 can be coupled to the system controller 126 and a system processor control and status 330 (FIG. 3), and system processor control, status, and data bus 332 which allows the system processor 128 to communicate with system processor storage 340 and the system controller 126 via a bi-directional control and data bus 129. The system processor 128 can use advanced analytics, predictive analysis, statistical inference and recommendation making as a basis for generating health science diagnosis and/or treatment. Advanced analytics is the grouping and synergistic use of techniques to improve domain understanding, to predict future outcomes and using statistical inference for decision making. The system controller 126 can be in communication with a UE 110.

The system processor 128 can offer other process benefits which can provide real-world technical benefits to a real-world technical deficiency within the art. For example, automating time-consuming aspects of processing that can include: 1) finding interactions among disparate data sources that can be difficult to detect, 2) providing objective and repeatable recommendations that can always "treat the same evidence in the same way", and/or 3) the data in Table 8—Prior Run Archive (shown below) can be made available anywhere in the processing.

Example Tables 1 through 9 can represent examples of input and output data and metadata that include the relationships, structures, patterns, time, location, other information, and reasoning for the HSDP 100 defined in this application. For example, Table 1 can provide individual medical information, such as available patient information including history. Information can be selected based on the current complaint(s) and/or provider (physician, diagnostic laboratory, hospital, etc.) visit and/or a chronic, ongoing complaint, condition and disease. Individual information can include personal information including genetic information and diseases (for example, simple gene disorders, genomic structural defects, copy number variants, etc.), medical history, examination results, treatments prescribed/discontinued, results of diagnostic testing performed, physician notes and follow up orders, etc. Note, all information in the individual entity can share one or more common attributes with other entities.

DNA sequencing, genotype, phenotype, gene and the protein made, biomarkers and nucleotide analysis can be performed as a source of further differentiation of the individual and/or origin of the disease. Also, Table 2 can provide information on blood-related relatives, if available. Tables 3 through 6 can provide a source of additional information for physicians and other professionals, diagnostic methods, diseases, treatments, which can share one or more common attributes with the individual(s) identified in Table 1. Publications offer a rich source of information. For example, meta-studies, such as those composed of various smaller studies, can offer larger sample sizes, which have been corrected for original study difference (i.e., normalized for population deficiencies, biases, etc.). These differences can be corrected using the methods, systems and apparatuses disclosed herein. Information presented in these tables can be very valuable in prescribing treatment for the individual identified in Table 1. These sources can provide valuable innovative diagnostic procedures, treatments, disease causes, etc.

Table 2 can include individual family history information. Table 3 can include physician information, example Table 4 can include other medical professions information, Table 5 can include hospital information, example Table 6 can include health related publications information, Table 7 can include pharmaceutical information, and Table 8 can include prior run archive information. One of ordinary skill within the art understands that such information from Tables 1 through 8 are examples of health science related information, and that Tables 1 through 8 can include any other health science information that can be used to make health science diagnosis and/or treatment. These inputs and outputs can be used to make recommendations in health science, for example, medical recommendations support, pharmaceutical discovery and epidemiological analysis and propagation, mutation of infectious diseases, or any other recommendations related to health sciences. Thus, the computer-based methods, systems and apparatuses disclosed herein can provide recommendations as applied to health science applications. The input and output data for various applications can be interrelated. Tables 1 through 9 can be linked both forward (e.g. individual to pharmaceutical drug) and in reverse (e.g. pharmaceutical drug to individual). Note that throughout this document individual and patient are used interchangeably.

Table 7 can provide information on all medications used by the individual in Table 1. This information can include 1) Pharmaceutical Name and ID 2) Manufacturer, manufacturer code, date code, physical characteristics, and manufacturing location, etc., 3) usage (diseases/therapies/disease specific therapeutic dosages/efficacy, metadata & history), usage can depend on the disease, individual genetics/DNA/RNA and current individual physiology and health status, 4) known side-effects and interactions with other drugs, genetics, procedures and food. These includes a complete analysis of all foods and supplements and can be dependent on the disease, individual genetics (e.g., genotype, phenotype, DNA, RNA, etc.) and individual current conditions, 5) drug interactions, side-effects, efficacies & sensitivities including dosages, individual physiology, genetics (e.g., genotype, phenotype, DNA, RNA, etc.) and health status, 6) synergistic & complementary drugs: diseases/therapies/disease specific therapeutic dosages/expected results, metadata & history. This drug information can be dependent on the disease, individual genetics/DNA/RNA (including types and functions), health status, current individual condition, etc. Note all information in these entities, such as individuals, drugs, treatments, etc., that are defined by feature vectors can share at least one common attribute. The more attributes that a particular entity shares (that is, have in common) with other entities in a particular decision hyper-volume, the higher the confidence of the decision and entity assignment to the particular decision hyper-volume. The decision hyper-volume is the defined multidimensional region that is enclosed by a multidimensional surface that identifies entities that share like attributes.

Figure 3:
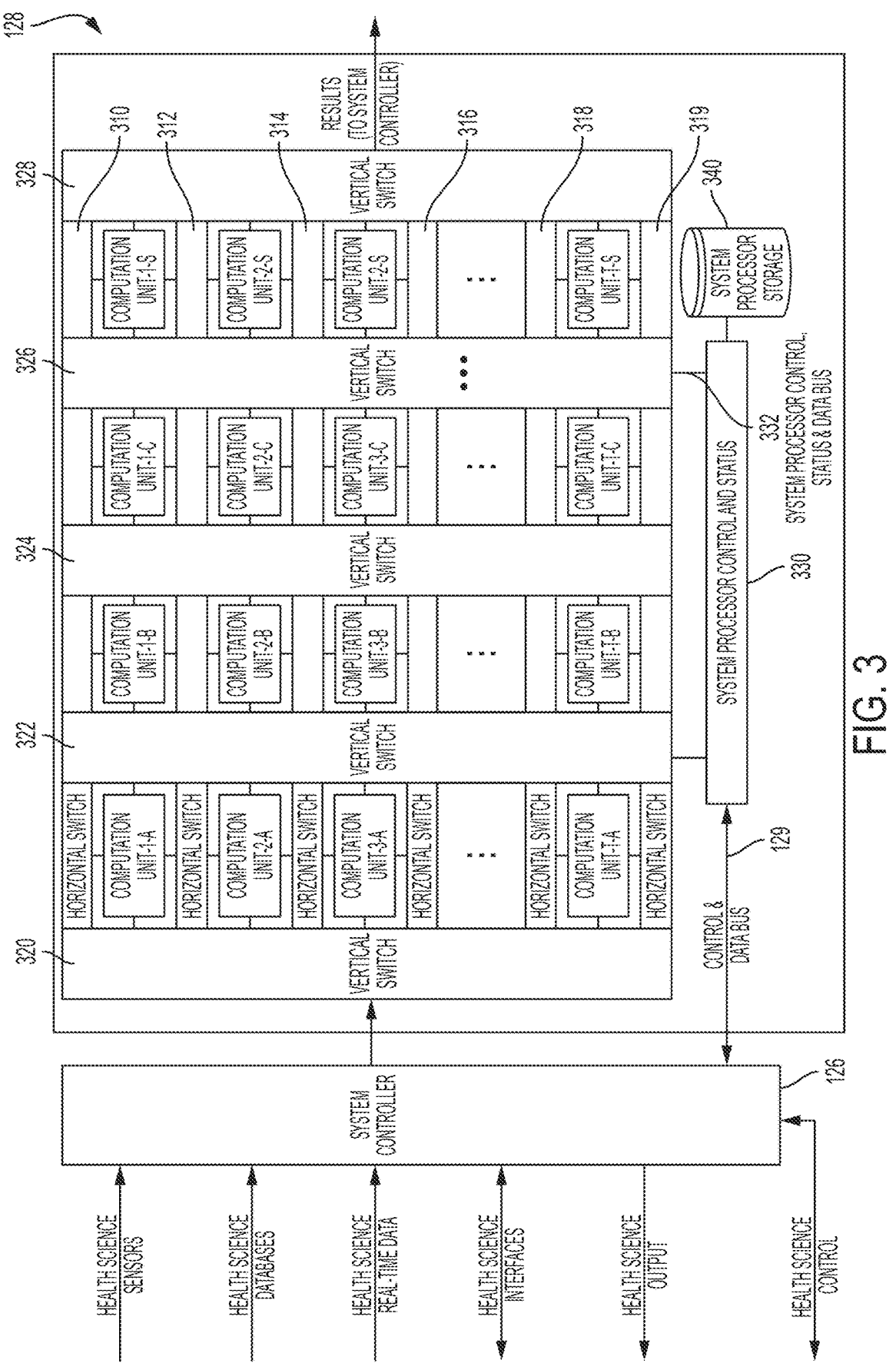
FIG. 3 illustrates an example system processor implementation, in accordance with one or more possible embodiments.

All input and/or output tables, such as Tables 1 through 9, can include data/metadata and/or graphical data (including maps, graphs, charts, etc.). For each application or combination of applications for such Tables, Table 8—Prior Run Archive can contain an archive of all input, metadata, graphical data, intermediate results, and output information associated with each processing run. This information can be stored in the system processor storage 340 (FIG. 3).

Using a multistage, iterative adjudication processing, any information in the output tables can be combined with any selected data/metadata in the input and prior run archive tables for any health science application. For example, medical recommendations result can be utilized in a subsequent drug discovery application. Data can be processed, in serial, in parallel and/or in combination of these. Data/metadata in any of the Tables 1 through 9 can be encrypted and/or randomized, as necessary, to ensure privacy (e.g. Health Insurance Portability and Accountability Act (HIPAA) Compliance). Data and/or metadata can be derived from any EMR system (for example, EPIC, Cerner, Allscript, government databases, etc.).

All data within Tables 1 through 8 can be updated over time and as medical science, medical technology, life science and the practice of medicine evolve (e.g., procedures, symptoms, treatments, pharmaceuticals, genetic treatments, and any combination of these, etc.). Data can be tracked over short intervals, as well as an individual's lifetime and/or over multiple generations (the tracking can be forward and backward). Also, data can be multi-scale, for example, DNA sequences, genes, cells, organs, species, and human, or a combination of these.

TABLE 1

Individual Medical Information

Individual Name (Aliases and dates) & ID
Record Number (0)
Addresses, (current, history and dates)
Date of Database Update
Occupation(s), living situation(s), and lifestyle choices (alcohol, tobacco, drug use, exercise type and amount, sleeping habits, socialization, etc.)
Environmental factors (e.g., chemical, biological, etc.)
Dietary factors (diet and food allergies)
Personal: Age, gender, ethnicity, race, blood type, height, weight, muscle/adipose tissue ratio, distribution of adipose tissue, joint health, blood pressure, blood sugar, blood panel, blood gases, eye disease and relationship to internal diseases, dental diseases and relationship to internal diseases, etc.
Family Links (relationships individual names and IDs)
Birth & Death Certificates (individual and family members)
Travel and/or exposure history (Individual, Family & Friends)
Medications (pharmaceutical name and ID, date code, characteristics (Define) period(s) of use), surgical procedures, immunizations, allergies histories
Medical history: dates, physician name(s) and ID, hospital name(s) and ID, complaints, diagnosis(es), diseases & pathologies, referrals and consultations
Medical/Surgical tests performed: dates, diagnostic procedures (e.g., OB/GYN, ophthalmology, psychiatric, cardiology, endocrinology, allergies, immune system, biomarkers, protein analyses, genetic sequencing, neurological, internal medicine and associated documentation)
Treatments prescribed (e.g., medical, surgical, medication, lifestyle changes, necessary follow up, and/or specialist referrals)
Hospitalization, dates, reason, all documentation (e.g., complaints, diagnostic procedures e.g., biopsies, pathology, medical testing, treatment plan, medications (changed and/or given), surgical and/or medical interventions, discharge summary, and necessary follow up)
Diseases: genetic diseases and treatments, complex, multiple disease and treatments (e.g., heart disease and diabetes, eye disease and diabetes, etc.)
Measurements from a wearable device. This data can exist in the wearable device, a computer system, a distributed computer system, a cloud based computer system, and/or a mobile cellular device.
Update any new and/or changes to individual and/or individual's family history data
Update any new and/or changes to existing conditions for individual and/or individual's family history data
Metadata for any changes detected from sensors (including diagnostic and diagnostic procedure imaging), tissue cultures from biopsies, autopsies, imaging studies, and real-time sensors

TABLE 1-continued

Individual Medical Information

Metadata for any changes detected from diagnostic procedure (genetic, medical and diagnostic procedure imaging), tissue cultures from biopsies, autopsies, imaging studies, and real-time sensors
Record (N)

TABLE 2

Individual Family History

Name & ID
Family Member (0): Name & ID, blood relationship to individual, living/dead, link to the Family Member (0) Individual Database and History (Table 1)
. . .
Family Member (N): Name & ID, blood relationship to individual, living/dead, link to the Family Member (N) Individual Database and History (Table 1)

TABLE 3

Physician Information

Name & ID (e.g.. National Provider Identifier (NPI))
Addresses, (current, and dates)
Credentials (e.g., MS, PhD, MD, OD, board certifications, regional medical licensing etc.)
Address history
Affiliations (e.g., hospital, medical school, professional societies, etc.): current and history
Patients seen per year in specialty and/or subspecialty, morbidity and mortality
Residencies, fellowships, and Post Doctorial
Publications, Conferences and citations
Research description and results, funding source, study dates, etc.
Recognition, Awards and Patents
Malpractice complaints, suits, Key Performance Indicators tracking, etc.

TABLE 4

Other Medical Professions

Name & ID
Affiliation (e.g., University, Research Laboratory/Institute, Government, Company, Consultant, etc.)
Addresses, (current, and dates)
Affiliation history
Education, Subject and Location (e.g., BS, MS, PhD, post-doctoral, RN, Technicians, etc.)
Domain Expert (or Subject Matter Expert): Anthropology, Psychology, Botany, Chemistry, Bioinformatics, Engineering, Pharmacology, Histology, Infection Diseases, Clinical Social Work, Sociologist, Computer Science, Neuroscience, nerve transmissions, circulatory system, public health, genetics, physiology, etc.)
Work history
Other Affiliations (e.g., hospital, medical school, professional societies, etc.): current and history
Publication, Conferences, citations, etc.
Research description and results, funding source, study dates, etc.
Recognition, Awards and Patents

TABLE 5

Hospital Information

Hospital & ID
Addresses, (current, and dates) for each location
Credential (e.g., Certifications, Licensing, Accreditations, Medicare, Medicaid, Insurance accepted, etc.)
Type: Community, Academic
Facilities: Emergency Department, ICU, PICU, Trauma Center and Levels, etc.
Specialties, subspecialties, number of beds, number of physicians, number and type of nursing and technicians (respiratory, physical therapy, imaging, laboratory, etc.)
Affiliations (e.g., hospital credentials, medical school): current and history
Patients seen per year in each specialty and/or subspecialty and morbidity and mortality
Residencies and fellowships and associated specialty
CMS Quality Measure Benchmarks
CMS Hospital Value-Based Purchasing

TABLE 6

Health Related Publications

Articles from world-wide, recognized and/or referred medical, public health, pharmacological and scientific journals, conferences and proceedings from Google-Scholar Library of Congress, FDA, NIH, NCI, CDC, WHO, etc. and other PUBMED-like publications (Links to physician, medical professional, and scientist name and ID)
Articles from world-wide, recognized and/or referred sources in cell biology, genetics, molecular biology, diseases, immune system, aging, viruses (lifecycle and/or mutations), bacteria (source, drug resistance, etc.) and clinical studies

TABLE 6-continued

Health Related Publications

Data from organizations that routine monitor status of infection disease (World Health
Organization, University Schools of Public Health, Center for Disease Control, etc.)
Articles from infectious disease journals and publications, Military publications, and other
applicable journals. Noting, Location and/or origin of outbreak, time of outbreak, interval of
outbreak, affected area, symptoms and other information regarding affected individuals
Articles and resources from the internet (e.g., HealthMap or HealthMap-like resource that
collects and integrates outbreak data from a variety of sources, including news media (e.g.,
newspapers, TV, Google-like news and searches), expert-curated accounts (e.g., ProMED
Mail), and other validated official alerts systems)
Metadata for patterns, causes, effects on health of population, disease conditions in population,
and genetic studies of hosts). And population not affected.
Metadata for demographic bio-monitoring, exposure data, origin of outbreak, location of
outbreak, genetics (DNA, RNA, etc.)
Metadata of outbreak, social graph of outbreak transmission vector based on location and
time, spread of outbreak as function of time, morbidity and mortality within population,
disease cause and effect within population
Metadata of symptoms of outbreak as a function of time, disease surveillance, forensic data
and history
Metadata for mutations of outbreak intra host and inter host, biological, chemical and
radiological studies on health (morbidity and mortality)
Metadata for mutations of outbreak intra host and inter host, biological, chemical, radiological
warfare studies on health (morbidity and mortality)
Case studies of single individual and groups of individuals, case control studies. Infectious
diseases and vectors
Metadata from monitoring social media and other sources.
Standards of Care (SOC)
Up-to-Date, Up-to-Date-like medical procedures, treatments databases, medical textbooks, etc.
Meta-studies (e.g., composed of various smaller studies)

TABLE 7

Pharmaceutical Information

Pharmaceutical Name and ID
Manufacturer, manufacturer code date code, physical characteristics, and manufacturing
location, etc.
Type: Brand name, generic, biologically similar and over-the-counter
Affected Human systems (e.g., brain, nervous system, endocrine, cardiovascular, pulmonary,
ENT, epidermis, etc.)
Genetic therapies and modifications (e.g., DNA modification, RNA modification)
Genetic editing and/or modifications (e.g., for cancerous tumors and other cancers, etc.)
Drugs to affect the immune system, cell systems, etc.
Drug delivery systems (e.g., exosomes (lipid-based), injection systems)
Chemical, biological and inert substances contained in drugs
Description & Markings
Chemical and biological active compound databases (proprietary and public domain)
Usages: Diseases/Therapies/disease specific therapeutic dosages/Expected Results, Metadata
& History. Usage can be dependent on the disease, individual genetics/DNA/RNA and current
individual physiology and health status.
Known side effects and interactions with other drugs, genetic procedures and food. These
include a complete analysis of all foods and supplements and can be dependent on the
disease, individual genetics/DNA/RNA and current individual condition
Drug Interactions, side effects, efficacies & sensitivities including dosages, individual
physiology, genetics/DNA/RNA and health status
Synergistic & Complementary Drugs: Diseases/Therapies/disease specific therapeutic dosages/
Expected Results, Metadata & History. This can be dependent on the disease, individual
genetics/DNA/RNA (including types and functions), health status, current individual condition
Synergistic & Complementary use with medical and surgical procedures: Diseases/Therapies/
disease specific therapeutic dosages/Expected Results, Metadata & History
Micromedex Database and Micromedex-like databases for Clinically focused (Drugs and OTC
medications)
Articles from world-wide, recognized medical and pharmacological journals, PUBMED,
conferences and proceedings from Library of Congress, FDA, NIH, NCI, CDC, NIMH, WHO,
etc. and other publications
Preliminary and final results from phase 1, phase 2 and phase 3 Government drug testing
Drug allergic reactions
Efficacy, morbidity/mortality of drugs based on the disease, patient genetics/DNA/RNA, health
status, current patient physiology
T-cell studies
Stem cell research
Anti-aging, immunotherapy, transplant rejection using cell and genetic modifications, etc. (e.g.
oncology, etc.)

TABLE 7-continued

| Pharmaceutical Information |
| --- |
| Enzyme production and applications |
| Vaccine development (using live and dead virus) & RNA mutations |

Table 8 represents Health Science Data and Metadata, Intermediate Results, and Output History that can contain all data and metadata derived from Tables 1-8 inputs and Table 9 outputs and their respective history for use in each health science application processed. Each health science application processed can have its own unique Table 8. The information contained in each Health Science Table 8 can be used for model building, forensic analyses, trending, change detection, inference and/or prediction based on NLM clustering and adjudication. An entity can be defined by a set of attributes (something belonging to an individual, medication, disease, treatment, diagnosis, etc. and/or groups of these, etc.) defining a point in multidimensional space.

TABLE 8

| Prior Run Archive |
| --- |
| Current Health Science Processing Run (0) ID |
| Run (0) Time/Date Stamp |
| Run (0) Input Data |
| Run (0) Graphical Information |

TABLE 8-continued

| Prior Run Archive |
| --- |
| Run (0) Metadata |
| Run (0) Intermediate Results |
| Run (0) Output Results |
| Run(0) Definition of Entity Universe axes and associated attributes |
| Run (0) Representation of all entities within the entity universe |
| . . . |
| Prior Processing Run ID (M) |
| Prior Processing Run results |

Table 9 represents an example of Health Science outputs that can be used for drug discovery, patient treatments, diagnostic procedures and genetic studies derived from the Health Science input Tables 1-8 defined in this application. Throughout Table 9, attributes, entities, groups of entities and/or sub-entities, as well as time and location can be utilized in further analysis and/or to refine recommendations. The Health Science outputs can be provided to pharmaceutical firms, health care professionals, researchers, government, patients, etc.

TABLE 9

| Health Science Outputs |
| --- |
| Diagnosis, reasoning and ranking based on a population with the same/similar attributes for entities |
| Recommended treatment, reasoning and ranking based on a population with same/similar attributes |
| Custom diagnosis (including genetic entities, environment and other factors), reasoning and ranking with a population with same/similar attributes for entities or groups of entities |
| Custom treatment (including genetic entities), reasoning and ranking based on a population with same/similar attributes for entities or groups of entities |
| Analyze morbidity and mortality using information for treatment and pharmaceuticals used |
| Discover relationships, structures, patterns and information using any and all attributes, entities, groups of entities and/or any combination thereof in for diagnosis and/or treatment of disease or condition. This can include primary, secondary, tertiary, etc. causes and effects and associated interrelationships. |
| Discover relationships, structures, patterns and information using any and all attributes, entities, groups of entities and/or any combination thereof in genetic/phenotype/genotype application for diagnosis and/or treatment of the disease or condition |
| Discover relationships, structures, patterns and information using any and all attributes, entities, groups of entities and/or combination thereof to find the utility of Smart Personal Sensors (smart devices that monitor, process, record and telemeter results, diagnostic testing and imaging studies to successfully diagnose and treat the disease or condition. |
| Discover relationships, structures, patterns and information using any and all attributes, entities, groups of entities and/or any combination thereof for medication side effects, drug-drug interactions, drug-food interactions, patient allergies, medication interactions and patient sensitivities based on population (e.g., genetics, environment, family history, physical characteristics, etc.) with same/similar inputs entities (for example, manufacturer, name brand, generic) |
| Discover new and/or improved medicinal compounds and/or drugs based on a population with same/similar attributes, entities and/or combinations thereof |
| Discover drug efficacies and therapeutic dosages (ranges) for different diseases based on a population (e.g., genetics, environment, family history, physical characteristics, etc.) with same/similar attributes, entities and/or combinations thereof |
| Discover and characterize biologically active compounds efficacies and therapeutic dosages for different diseases based on a population with same/similar attributes or combinations thereof (including genetic and phenomic information) |
| Discover drug efficacies and therapeutic dosages (ranges) for different diseases based on a population with the same attributes or combinations thereof (and containing certain active and inert biological and chemical compounds and ingredients) |
| Discover relationships between any entity, groups or subsets of entities and combinations of active biological/chemical compounds and medical condition/diseases, and/or |

TABLE 9-continued

Health Science Outputs combinations of these

Discover relationships between any entity, groups or subsets of entities and combinations
of active biological/chemical compounds and efficacy, morbidity/mortality /disease,
patient genetic and phenomic data, and/or combinations of these Discover relationships among any entities, groups, or subsets of entities and/or
combination thereof (including drug sensitivities, allergies, addictions and patient
attributes)

Discover relationships between any attribute, entity, or groups or subsets of entities and
associated epidemics both natural and man-made, transmission characteristics and
vectors, location and timeline, origination, spread, mutation characteristics, symptoms,
hosts and genetics of hosts, mutations intra and inter host DNA and/or RNA.

Discover relationships between any attribute, entity or groups or subsets of entities to
evaluate and analyze of all methods to control and contain outbreaks, diagnose and treat
effected individuals, and monitor the spread of outbreak Discover relationships, structures, patterns and information of any attribute, entity, group
or subset of entities to any attribute, entity, group or subset of entities. This can be
between an individual attribute, entity, group or subset of entities and clusters and any
combination thereof.

Figure 2:
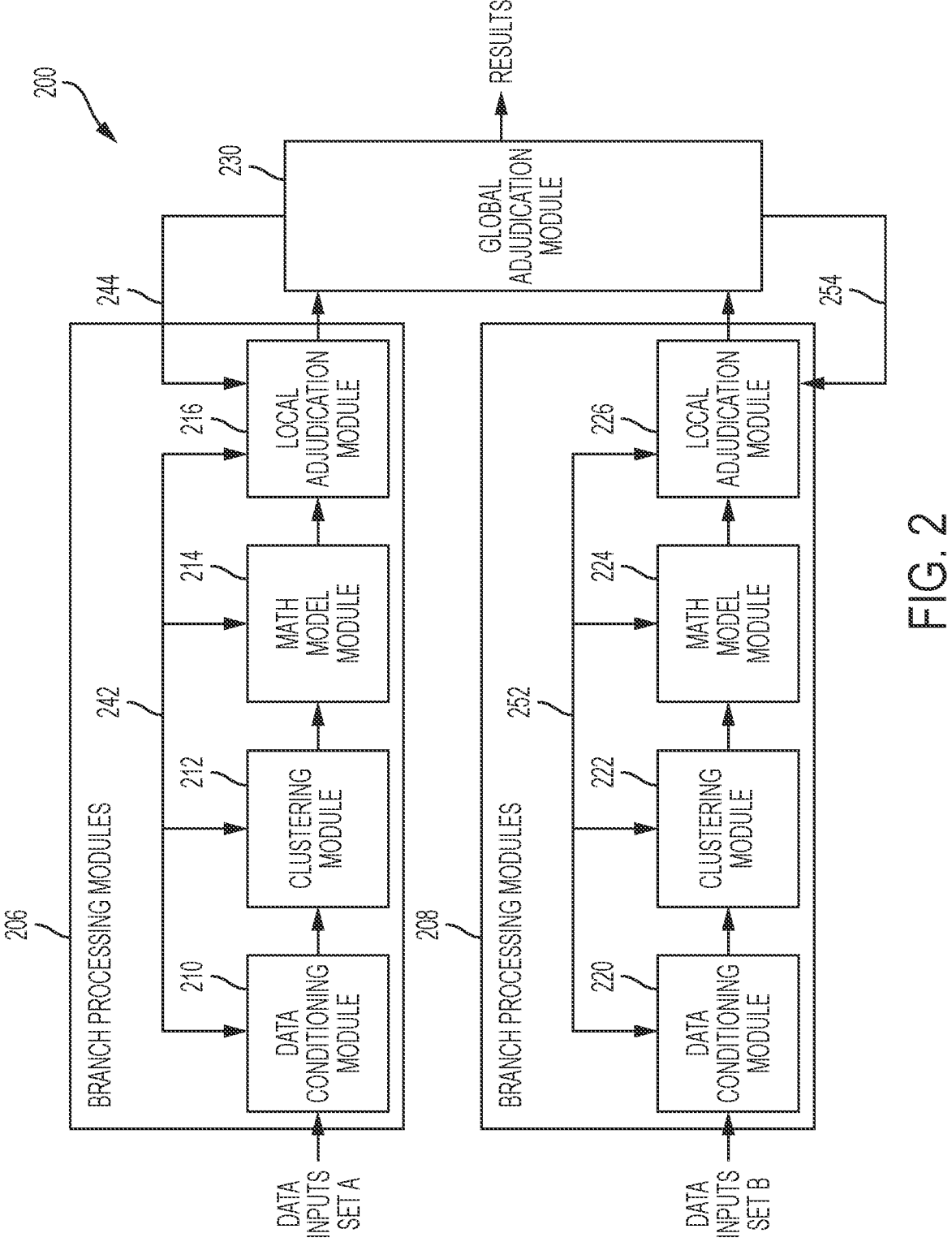
FIG. 2 illustrates an example advanced analytics method, in accordance with one or more possible embodiments.

Recommend diagnosis(es), treatment(s) and potential side effects, etc. with reasoning and
rank order based on a confidence region Discover structures formed by the DNA and the impact on health, aging, cell mutation
and reprograming of DNA to strengthen immune system, understand and control cancer
growth, and understand and treat diseases Drug cost optimization based on potential market size (number of patients with need,
development cost, projected market share and potential ROI FIG. 2 illustrates an example advanced analytics method 200, in accordance with one or more possible embodiments. The processes in the advanced analytics method 200 can be performed by the system processor 128 and can be categorized into four blocks: data conditioning, clustering, mathematical modeling, and adjudication. The two branches of the advanced analytics method 200 shown can include data conditioning modules 210 and 220, clustering modules 212 and 222, math model modules 214 and 224, local adjudication modules 216 and 226, respectively, and global adjudication module 230. The specific data and processing selected for each block can be controlled within a processing branch (intra-branch) by the local adjudication module 216 and 226 and across processing branches (inter-branch) by the global adjudication module 230. The combination of local adjudication 216 and 226 addressing the branches and operating in conjunction or separately with the global adjudication module 230 is referred to the adjudication process throughout this document. All intermediate and final information from current and prior processing can be placed in the system processor storage 340 (FIG. 3). The advanced analytics method 200 can be implemented in a highly parallel architecture, such that any and/or all of these techniques can be performed serially or simultaneously in parallel on any individual data set, any group of selected data sets and all data sets in any combination. The processing flow of the advanced analytics method 200, shown in FIG. 2, can be performed by the system processor 128. The individual blocks of the system processor 128 can be partitioned between and operate simultaneously in, one or more of the following implementations: local computing, mobile computing, distributed computing, cloud-based computing, Graphics Processing Unit (GPU), array processing, Field Programmable Gate Arrays (FPGA), tensor processor, Application Specific Integrated Circuits (ASIC), quantum computing, as a software program or "app", any combination of these computing environments (e.g. where a computer has one or more GPUs, tensor processor, etc. operating as processing accelerators), or another implementation that allows for simultaneous operation of individual blocks of the system processor 128. For example, the system processor 128 and/or the system controller 126 can operate as an "app" on a tablet or smart phone. In at least one embodiment, the system controller 126 and the system processor 128 can be combined into a single computational unit.

The use of this tight coupling of processes together with both local and global adjudication processes performed by the local adjudication modules 216 and 226, and global adjudication module 230, respectively, provide several advantages. This coupling can produce a tractable representation to support analysis that makes the best use and optimization of all data.

The implementation and architecture of the system processor 128 is easily extensible and highly scalable through parallelization and can allow all proprietary and/or private data/information to be segregated from other data/information within the system processor 128. The proprietary and/or private data/information can be isolated during processing by the system processor 128 without affecting any other data and/or information. Selected information can be encrypted and/or randomized and can meet or exceed all privacy (including HIPAA) requirements.

Depending upon the condition of the retrieved dataset, that is if the retrieved data needs to be conditioned prior to processing by the clustering modules 212 and 222 the data conditioning modules 210 and 220 can formulate the entity by performing preprocessing, text processing, data compression, data reduction, dimensional reduction, etc. from the retrieved dataset. The data conditioning modules 210 and 220 can process the data from Tables 1 through 9 as data sources that can be applicable to the HSDP 100. In an alternate embodiment, the entity can be formulated in advance of, instead of immediately before, being used by the respective clustering modules 212 and 222. In at least one embodiment, this advanced entity can be formulated with a processing unit outside of the HSDP 100, distinct from the data conditioning modules 210 and 220. Examples of data types can include, but are not limited to, text, alphanumeric, biological sequences, chemical sequences as well as meta-data for images, charts, tables, symbols, maps, locations, graphics, video, etc. The system can accommodate new sources of health science data as it becomes available using the same processing techniques. The data conditioning modules 210 and 220 can accept analytics inputs data sets A and B, respectively where data sets A and B can share the same data (and can, in fact, be the same data). The data conditioning modules 210 and 220 can perform the same and/or different data conditioning on the inputs data sets A and B, respectively, and can output conditioned data to the respective clustering modules 212 and 222.

Among other operations, the system processor 128, implementing the data conditioning modules 210 and 220, can unify sensor metadata and databases associating unstructured text information for each. By using a common term space for the entity, unification can produce a congruent representation for entity. Note, any data can be structured text, such as a sentence, a paragraph, a document, etc., and unstructured text, such as a word, a formula, a mathematical sequence, combinations of these, etc.

The data conditioning modules 210 and 220 can perform the following preprocessing operations that include, but are not limited to, data consistency or conformance checks, tag data, data compression, data alignment, and any corrections, modifications, repairs and/or replacements of missing or out-of-bounds data. The data conditioning can be beneficial to performance and subsequent operation of the system processor 128. Since not all data can be in a numeric format, any alphanumeric or other input data types can be re-encoded by the data conditioning modules 210 and 220 into a numeric representation. Functions performed by the data conditioning modules 210 and 220, such as corrections, modifications, repairs and/or replacement of missing or out-of-bounds data, can be tagged for subsequent analysis for deviation from the original data. The conditioning performed by the system processor 128 and applied to the input data can include, but is not limited to techniques from statistics, information theory, and pattern recognition, as well as other approaches for filtering imperfect data. Based on the input data, the data conditioning performed by the data conditioning modules 210 and 220 can be selected and controlled by the adjudication modules 216, 226, and 230.

The data condition modules 210 and 220 can perform text processing that can include Term Frequency-Inverse Document Frequency (TF.IDF), Syntactic, and Sematic processing. Each are discussed subsequently in more detail. The data condition modules 210 and 220 can perform a feature extraction technique that can be used in text processing to improve the speed of performance and convergence of the clustering. For example, text processing (structured and unstructured) can include Information Theoretic (e.g., the TF.IDF), Syntactic and Semantic processing associated with all retrieved datasets and/or a combination of these (each method is subsequently discussed). These techniques can be used to study the biological and chemical sequences as well as other sequences in structured and/or unstructured sources. The data condition modules 210 and 220 can perform other techniques that can also be used to numerically encode such text and/or sequences, such as distributional semantics (e.g. distance between terms, DNA sequences, RNA sequences, etc.), latent semantic, computational linguistics, indexing, text mining, statistical semantics, Principal Component Analysis and Factoring, histogram generation, multidimensional correlation, etc. In an example, the system processor 128 can formulate the entity using text processing including performing at least one of Information Theoretic, semantic, and syntactic, the entity formulation can include extracting numerically encoded text features from at least one of bulk text, structured text, unstructured text, biological sequences, chemical sequences, deoxyribonucleic acid, and ribonucleic acid. The system processor 128 can perform the text processing to eliminate at least one unproductive attribute and at least one unproductive entity in nonproductive regions of an entity universe using a loss function.

The data conditioning modules 210 and 220 can use information theoretic, syntactic and/or semantic processing methods. These methods can be used independently, in parallel, in series or in combination to reduce the dimensionally of a high dimensional vector space under the control of the multistage adjudication described herein. At least one embodiment uses Term Frequency, Inverse Document Frequency (TF.IDF) methodology and multiple pairwise Cosine Distances between documents to extract numerically encoded text features from bulk, unstructured text of the retrieved dataset. The Cosine Distance (vector dot product between documents) is a measure of similarity between two term vectors that measures the cosine of the angle between them and can be used to drive the attraction/repulsion in the clustering process.

The data condition modules 210 and 220 can perform the TF.IDF process that can generate or modify term vectors formed in the data conditioning modules 210 and 220, with the TF.IDF being a metric that assigns numerical values to unstructured text. A term vector can be a multidimensional vector of alphanumeric features (where terms are the dimensional axis) that represent a document. The data condition modules 210 and 220 can numerically encode these term vectors using the TF.IDF. Document sources, such as all documents that make up a document corpus for the retrieved dataset, can be, e.g., newspapers, magazines, journals, government documents, social media, wiki's, blogs, and/or any other textual sources. TF.IDF can be grammar and/or language agnostic, and can be applied to text in any language, without requiring that the text be translated. The construction of TF.IDF scores and structures, can operate the same for all text in any written language, whether alphabetic (e.g., American English) or iconographic (e.g., Traditional Chinese). Even artificial term spaces, such as chat speak ("lol", etc.), hash tags (#prom), and emoticons (e.g., smiley face) can be utilized in the TF.IDF processing. The data condition modules 210 and 220 can compute the TF.IDF across the document corpus by counting terms in a document, counting the number of documents in the document corpus, and counting the number of documents for a given term, generating a TF.IDF score. The TF.IDF score can be then calculated from these terms. The TF.IDF scores for all terms can be log-normalized for ease of use. When documents are added or removed from the document corpus, the data condition modules 210 and 220 can updating the term scores by only adjusting the frequencies for the affected terms. The data condition modules 210 and 220 can perform matching using keywords from queries, profiles, recommendations, and histories.

The system processor 128 need not use all the terms associated with the document corpus to determine a term score. By sorting the TF.IDF term scores within the corpus of documents, the system processor 128 can perform a match on only the "best" terms within the corpus, that is those having the highest TF.IDF use. The selected terms can be the most sensitive and discriminating terms across the corpus of documents, thus giving both high sensitivity and specificity (each defined subsequently) to later processing.

The system processor 128 can use the TF.IDF processing to generate a term vector for a document based on the term score of each selected term associated with the document. Terms can be space-delimited character strings (words), but other term definitions can include phrases, numbers, names, DNA sequences, etc. Measuring similarity between two documents based on their respective term vectors can be done in several ways, as discussed subsequently. It is important to note that not all terms in a document will convey the same amount of information.

A set of all terms that occur anywhere in any document can be represented by the equation W={$w_1$, $w_2$, . . . , $w_L$}, with $T_i(w_j)$ being equal to a number of times term $w_j$ occurs in document i. From this, the system processor 128 can determine the total number of times a term occurs, counting multiplicities, in the entire document corpus D by adding the occurrences in each document.

The data condition modules 210 and 220 can use one or more of a commonly used set of strategies for selecting terms that can include document distance and similarly which disregards grammar, instead regarding each document as a collection of terms. These collections are routinely called "Bags of Words", and the strategies "Bag of Word" strategies. Examples of such strategies can include:

| | |
|---|---|
| Strategy 1 | Documents i and j are similar if, and only if they both contain all of the terms (selected term list). |
| Strategy 2 | Documents i and j are similar if each contains at least N of the terms in a given selected term list, where N is an adjustable parameter. |

The stringent match criterion of Strategy 1 will generally give few false alarms, but will also miss many similar documents. Strategy 1 is specific, but not sensitive. The looser match criterion of Strategy 2 will generally recognize similar documents (along with generating many false alarms). Strategy 2 is sensitive, but not specific. A selected term is "good" for characterizing document content if that document uses the term multiple times. This is because a term that a document uses frequently is likely to be related to what the document is actually about. This makes the match more sensitive to those documents most likely to be relevant. The adjustable parameter, N, can be limited as increasing N provides marginal improvement of document to document sensitivity and specificity. Since the number of selected terms defines the dimensionality of the term vectors, a limit on N can be an initial process in limiting the dimensionality in the health science processing.

A selected term can also be "good" for characterizing document content if it occurs in most documents that are relevant to a specific concept, condition, and/or entity, but it does not occur in documents concerning unrelated topics. This will enable the selected terms to be used to detect and ignore irrelevant documents, making the match more specific (sensitivity). The perfect selected term(s) for characterizing a document would occur many times in that document, and nowhere else (specificity). This is achieved by combining two sub-metrics: one for sensitivity and one for specificity.

A good match term $w_j$ for a document $d_i$ will have a large TF and a small DF. TF and DF can be combined into a single metric by taking a ratio where the "large=good" sub-metric TF is in the numerator, and the "small=good" sub-metric DF is in the denominator. To avoid carrying around a complex quotient of fractions, the quotient can be a product of TF with the reciprocal of DF, referred to herein as the Inverse Document Frequency (IDF). A term's IDF value can be quite a bit larger than its TF values.

$$\text{Total count of occurrences of term } w_i = \sum_{k=1}^{M} T_k(w_i)$$

18 is larger than its TF values. Because of this, the logarithm of DF can be taken as an alternate approach to control its magnitude so that it doesn't "overwhelm" TF, resulting in the equation as follows:

$$\log(IDF) = \log\left(\frac{M}{DocCount(w_j)}\right)$$

Since there is no need to compute DF for terms that do not occur in any document in D, $DocCount(w_j)$ will always be at least 1. The TF.IDF term score can be defined as:

$$TF.IDF_{i,j} = (TF(w_j, d_i))(IDF(w_j)) = TF(w_j, d_i)\log\left(\frac{M}{DocCount(w_j)}\right)$$

To measure a keyword's sensitivity to a specific document, the system processor 128 can proportion all occurrences of a term that are in that one document. This can be referred to as the Term Frequency (TF) for that term and document and is defined below. The Term Frequency for term j in document i can be:

$$TF_{ij} = \frac{T_i(w_j)}{\sum_{k=1}^{M} T_k(w_j)}$$

In other words, $TF_{ij}$=# of times $w_j$ appears in document i/# of times wj appears in all documents.

The Term Frequency is a real number between 0 and 1 inclusive, and is zero for documents in which the term does not occur. If there are lots of documents, TF will be a very small number for most terms and a larger number for rare terms. If a term occurs in only one document, its TF will be 1 for that document, and 0 for all other documents.

In at least one embodiment, the TF.IDF processing can apply Synonym Annotation (i.e. using a single common term for synonyms) and making our terms that are of little value such as articles, adverbs, conjunctions, interjections, etc., to documents to accelerate the TF.IDF processing. This process can be used for dimensionality reduction for the term vectors. The Synonym Annotation can be used to accelerate genetic sequence processing.

Prior to TF.IDF processing, the data condition modules 210 and 220 can mask out any terms that occur in many documents that do not provide significant discriminating for any particular topic. Examples of these terms are:

| Parts of speech that are usually poor choices as match terms | |
|---|---|
| Part of Speech | Examples |
| Adverbs | quickly, as |
| Articles | a, an, the |
| Conjunctions | and, but, however |
| Interjections | hooray, ouch |
| Prepositions | on, over, beside |
| Pronouns | she, you, us |

These are related to the notion of "stop-words", that are poor stand-alone search terms.

The specificity of a matching term for a corpus D of documents measures whether the occurrence of that term is concentrated in a small percentage of the documents, or found in many of the documents. The Specificity can be computed as the proportion of all documents that contain the term.

Specificity can be represented as follows:

$$A(w_j, d_i) = 1$$

if term $w_j$ occurs in document $d_i$, 0 if it does not

The total number of documents among the M documents in $D=\{d_1, d_2, \ldots, d_M\}$ that contain term $w_j$ is then given by:

$$DocCount(w_j) = \sum_{k=1}^{M} A(w_j, d_i)$$

Then, the proportion of all documents that contain the term is given by the Document Frequency (DF) for $w_j$:

$$DF(w_j) = \frac{DocCount(w_j)}{M}$$

The Document Frequency is a real number between 0 and 1, inclusive. If the Document Frequency is one, the term occurs in every document. It will be smaller number (that is less than 1) for terms that occur in few documents. If a term occurs in NO document, its DF will be 0 for all documents.

The entity universe can have thousands of dimensions (e.g., a dimension can be a single attribute, a weighted attribute, a summation of weighted attributes, etc.). The system processor 128 can select the dimensionality of the embedding space, the number of dimensions input and/or the number of dimensions output, as a basis for trading accuracy for computational efficiency with the goal of minimizing the number of dimensions used in subsequent processing by the system processor 128.

Ambiguity can measure the comprehension of language and sequences using context and/or structure. Ambiguity can include local and global structures and components of sequences, which follow know and/or discoverable rules. Local ambiguity of can persist for short periods of time and/or short sequences of structured text, unstructured text and/or alphanumeric sequences, for example, DNA, RNA, chemical and biological representations which follow rules. Global ambiguity of can persist for long periods of time and/or long sequences of structured text, unstructured text and/or alphanumeric sequences, for example, DNA, RNA, chemical and biological formulations which follow rules.

The system processor 128 can perform syntactic processing that can measure local and global components of ambiguity, their length, their repartition interval/distance, their group repartition interval/distance and the sequence structures and/or rules of construction, respectively. Syntactic processing architectures can include serial and/or parallel processing. Serial processing tries to interprets the structure of a given text and/or sequence considering one interpretation at a time independently. Parallel processing tries to interprets the multiple structure and meaning of texts and/or sequences and to rank order these interpretations. Syntactic process can include many models, such as Garden path model, Minimal attachment, Constraint-based, and Computational modeling, etc. To facilitate dimension reduction and feature synthesis, each raw sparse vector of terms can be segmented into syntactic blocks (groups of terms having similar form [e.g., tables] or type [e.g., different languages, emoji's, chat-speak]), and/or into semantic blocks: groups of terms having similar function or meaning, e.g., emotive terms, technical terms, etc. Each of the raw text vector segments can be synthesized/encoded into a relatively small number of numeric scores.

The data condition modules 210 and 220 can perform other semantic processing methods independently, in parallel, in series or in combination to reduce the dimensionally of a high dimensional vector space under the control of the multistage adjudication. In at least one embodiment, semantic processing names are not used explicitly but rather semantic context can be used to implicitly define meaning. Ambiguity can measure the comprehension of terms, sequences and alphanumeric sequences. The use of semantic processing can be used to identify artifacts within sequences. These artifacts can be caused by noise, measurement errors, missing data and more importantly, the effects of mutations/aging/etc., and/or a combination of these.

The data condition modules 210 and 220 can form intermediate vectors on an original unaltered term vector, can be generated by subdividing term vectors, can be generated by combining one or more weighted term vectors, or can be a combination of these. The weighting of the term vectors to generate the intermediate vectors can be determined in the adjudication modules 216, 226, and 230. The adjudication modules 216, 226, and 230 can determine feature vectors by combining multiple intermediate vectors that represent an entity. An example of combining multiple intermediate vectors could be using social media text analysis and DNA sequences, RNA sequences and/or proteins, lipids, etc. string analysis that can be processed separately.

In addition, the adjudication modules 216, 226, and 230 can generate feature vectors, whether from one or multiple intermediate vectors, by appending parametric data dimensions. Examples appended parametric data dimension can include height, weight, and/or blood pressure. This appended information can include information and/or attributes, and/or derived information and/or attributes information contained in the health science specific Tables 1 through 9 and can increase the dimensional of the feature vector as compared to the intermediate vector. This appended information can be conditioned using other methods and techniques previously discussed in this disclosure or can be used as is. The creation of the feature vectors can be controlled by the adjudication process described herein.

The adjudication modules 216, 226, and 230 can tag and generate a feature vector by adding one or more tags to the feature vector. A tag can be numeric, alphabetic, alphanumeric tags, and/or symbolic. The tag(s) can be used to provide a map to the original information source and/or indicate that the feature vector was limited, synthesized, or in some way altered in the data preprocessing. Note tags be used for privacy and HIPAA compliance.

Feature vectors (tagged or untagged) can define the set of entities that are used in subsequent processing. Attributes can be considered characteristics that are used in the definition of an entity. Attributes (or unit vectors that span the multidimensional space) can define the entity universe axes. Weighted attributes can be combined to form new dimensionality unit vectors under control of the adjudication process described herein. Throughout the rest of the processing, the feature vectors are referred as entities in the universe. The feature vectors may be unaltered term vectors, intermediate vectors, and/or feature vectors with appended parametric data. In addition, that feature vectors may be tagged or untagged. The data conditioning modules 210 and 220 can perform dimensionality reduction to simplify subsequent processing with minimal acceptable loss of information contained in the data. Also, the dimensionality reduction can 1) compress/combine attributes, 2) can weight attributes, 3) eliminate regions of the entity universe containing sparse feature vectors and/or 4) masked and/or combinations of masked and/or combinations of unmasked and masked attributes. The dimensionality reduction can be done with term vectors, intermediate vectors, and/or feature vectors. Biomedical data (e.g., genotype-phonotype studies) is often high dimensional but sparse. Therefore, the dimension reduction techniques used below in combination with other attributes can be extremely valuable.

Dimensionally of the vector space can be reduced/increased using information loss/gain as a controlling factor. The information loss using Principle Component Analysis (PCA), Singular Value Decomposition (SVD) and/or State Vector Machine (SVM). Also, dimension reduction can be calculated by comparing the mutual information of the high dimension vector space, X, to the lower dimension vector space, Y, $I(Y;X)=H(X)-H(X|Y)$, where $H(X)$ is the entropy of X and $H(X|Y)$ can be considered as the variance loss. This approach can be generalized, that is, if Y explains the variance of X, the mutual information increases and/or decreases. Therefore, mutual information can be directly related to explained variance. This embodiment can allow the use of all aspects of entropy in the context of mutual information to calculate information loss and gain. The data conditioning module 210 and 220 can reduce the number of dimensions by compressing and mapping P feature vectors onto an S dimensional term vector-space (e.g., where S can of a very high dimensional vector space with the minimum loss of information under control of the local adjudication modules 216 and 226.

The system processor 128 can perform, in the data conditioning modules 210 and 220, vector weighting under control of the adjudication modules, 216, 226, and 230. The vector (and attribute) modification can include masking and/or weighting, adding a constant, multiplying by a constant, a unit axis, such as an attribute or combination of attributes. These operations can be done with term, intermediate, and/or feature vectors. The vector weighting can be controlled by the adjudication process described herein. Note, each dimension of a vector can be weighted separately and can include any value. Note, the feature processing, dimensionality reduction, and weighting can be performed by the system processor 128 in any order.

In an example embodiment, in which Document i and Document j can characterize some combination of text sequences. In at least one embodiment, a document can be a gene, chromosome, and/or other DNA/RNA sequence(s). Examples of a term k can be a word, phrase, DNA sequence, and/or chemical formula. Documents i and j can include an individual's medical information, related health publications, drug and/or treatment research, etc.

The affinity expression, $D^2(i, j)$, can be composed of at least one of Information Theoretic (e.g., TF.IDF), Syntactic, and Semantic terms. These terms can be used independently, in parallel, in series or in combination. The affinity expression can be considered a distance. Note that distance is used interchangeably in this specification with metric and metric distance and/or cosine distance.

The affinity between Document i and Document j can be defined by the exemplary equation as follows:

$$D^2(i, j) = \left\{ \sum_{k=1}^{Terms} [TF.IDF(i, k) - TF.IDF(j, k)]^2 \right\} + \{\tau(i) - \tau(j)\}^2 + \{v(i) - v(i)\}^2$$

$$\text{(Information Theoretic Term)} \quad + \quad \text{(Syntactic Term)} \quad + \quad \text{(Semantic Term)}$$

be less than P). The multistage, iterative adjudication structure/architecture can select and control dimension reduction via the local adjudication modules 216 and 226. In at least one other, the information loss using PCA, SVC, and/or SVD dimension reduction can be controlled by minimizing the loss function (defined subsequently) in the adjudication process described herein. Other methods for reducing the dimensionality of the term vector can include the loss function, expected loss, and/or neural networks. These methods are discussed in the clustering and adjudication processing. In an example, the system processor 128 can performs adjudication to minimize the loss function in order to optimize assignment of the entity by adjusting a decision boundary of the decision hyper-volume.

The data conditioning modules 210 and 220 can perform pruning using text processing to eliminate unproductive attributes and entities in nonproductive regions of the universe using loss function (subsequently defined). The data conditioning modules 210 and 220 can use any and all of these techniques in combination.

Calculating metric distances and vector angles in a high dimension space to discern useful information can fail using traditional clustering techniques due to the sparse data that cause ineffectiveness and inefficiency. The data conditioning modules 210 and 220 can perform dimensionality reduction where:
TF.IDF (i, k)=TF.IDF score of term k within Document i
TF.IDF (j, k)=TF.IDF score of term k within Document j
$\tau(i)$=average word count of the posts within Document i
$\tau(j)$=average word count of the posts within Document j
$v(i)$=average nuance of the terms within Document i; and
$v(j)$=average nuance of the terms within Document j.

The individual components, Information Theoretic (e.g. TF.IDF, bag of words, distance between words, etc.), Syntactic, and Semantic terms can be separately weighted. The $D^2(i,j)$ values can be used to drive the entity attraction and repulsion in the clustering process (subsequently defined). In an example embodiment, the use of computational linguistics, that is, TF.IDF and clustering, and can include linear clustering, nonlinear clustering, linear manifold clustering and/or nonlinear manifold clustering, can be applied by the system processor 128 to querying the available sensor and database information. This querying can be performed using natural language. A query or group of queries can be treated as a document and processed using the term processing and the linear, nonlinear, linear manifold, and/or nonlinear manifold clustering. Using the concept of "nearness", or a small metric distance between entities, also referred to herein as affinity, similarity, and closeness, new decisions can be made in the adjudication modules 216, 226, and 230. These identified entities can be used to create new, more effective and/or less costly decisions boundaries. The concept of "distant" (also referred to herein as dissimilar, not like, and other synonyms of distant) can also be used to eliminate or rank lower decisions. The $D^2(i,j)$ values can be used as a direct input to neural processing in the math model modules 214 and 224.

A cosine distance, using the TF.IDF method, can be a measure of similarity between documents and/or entities retrieved by the system controller 126. This cosine distance metric can be treated as a measure of angular distance between the entities and/or documents being described. For example, if two entities are "near" each other in terms of space defined by TF.IDF, the entities are more likely to be similar than dissimilar.

Information Theoretic (e.g., TF.IDF), Syntactic and Semantic processing by the system processor 128 can be used to study the structures formed by the DNA and its impact on health. These techniques can be used to analyze DNA mutations, aging and variations associated with other structures (e.g., chromosomes, genes, gene expression, proteins, immune responses, cell biology, etc.).

Term features (e.g. metadata) associated with sensors, and databases and other health science application textual corpus (e.g., chemical formulas, DNA structures and RNA structures) can include those drawn from bulk text from online sources, published articles, wiki's, blogs, social media content, etc. Information can be drawn by the system processor 128, through the system controller 126, from these sources to enrich the representation of entities.

Information Theoretic (e.g., TF.IDF), Syntactic and Semantic processing performed by the system processor 128 can be used to study RNA (ribonucleic acid), and its impact on health. These techniques can be used to analyze RNA mutations and variations associated DNA sequences. RNA is the messenger to carry instructions from DNA to control the synthesis of proteins, etc. In some viruses, RNA rather than DNA carries the genetic information. RNA can cause the reprogramming of and/or changes to DNA. This reprogramming can cause cell mutations thought to be responsible for aging, immune responses changes, and diseases. Virus RNA can be used for immunotherapy and for oncological and other applications.

For example, Information Theoretic (e.g., TF.IDF), Syntactic and Semantic processing can be used to study the genotype and phenotype and their impact on health. Genotype refers to the genetic makeup of an organism. Phenomes are the expression of entities in a cell, tissue, organ, organism and species. Genotype and phenotype can be used to classify traits using other observable attributes.

Attributes or combinations of attributes can be weighted and/or masked and/or combined to highlight one or more dimensional axes to enhance health science recommendations, e.g., diagnostic procedures, treatments, drug discovery, drug-drug interactions, and epidemiological studies. The weighting and/or masking and/or combination of these can be controlled by the adjudication modules 216, 226 and 230.

The clustering modules 212 and 222 can perform clustering, visualization, and data seeding functions. The clustering modules 212 and 222 can take the data received from the data conditioning modules 210 and 220, respectively, and output processed data to the math model modules 214 and 224, respectively. The clustering modules 212 and 222 can perform different types of linear, nonlinear, and linear manifold and nonmanifold clustering for use in the math processing modules 214 and 224 and adjudication modules

216, 226, and 230. Multiple implementations for forming the linear, nonlinear, linear manifold, and/or nonlinear manifold clusters can include tensor analysis, vector analysis, differential geometry, and spectral analysis. For example, in at least one embodiment vector analysis can be employed. Types of linear, nonlinear, linear manifold, and nonlinear manifold clustering can include linear classifier, nonlinear clustering, nonlinear manifold clustering, nearest neighbor classifier, fuzzy clustering, K-means clustering, K-profile clustering, spectral clustering, neural networks and Nonlinear Dimension Reduction (NLDR) methods, etc. NLDR methods can be used in Riemannian manifold learning.

The linear manifold (LM) clustering can use locally linear and/or locally nonlinear high-dimensional spaces that are embedded on a linear manifold. The nonlinear manifold (NLM) clustering can use locally linear and/or locally nonlinear high-dimensional spaces that are embedded on a nonlinear manifold. Various implementations of nonlinear manifolds can be utilized for multidimensional nonlinear manifold clustering on at least one element of the retrieved dataset, assignment of an entity into a decision hyper-volume based on the multidimensional nonlinear manifold clustering, and determination of the recommendation of at least one of health diagnosis and treatment for the patient based on the assignment of the entity into the decision hyper-volume.

The nonlinear manifold clustering can improve the probability of detection of the similarities and differences within a given data set while reducing the probability of false alarm by using locally linear and/or locally nonlinear high-dimensional spaces that are connected via a nonlinear manifold. That is, nonlinear manifold clustering allows for a reduction of a highly nonlinear problem to a set of locally linear and/or nonlinear decision hyper-volumes. In an example, the utilization of the multidimensional nonlinear manifold clustering further includes utilizing the multidimensional nonlinear manifold clustering and at least one other type of multidimensional clustering including at least one of linear clustering, linear manifold clustering, and nonlinear clustering.

The system processor 128 can derive a set of conformed, that is mathematically well behaved, feature vectors in an N-dimensional Euclidean space, which can be viewed as a Hilbert Space, called the embedding space, from the input data in Tables 1 through 9, and any subset and/or combination thereof. Within the embedding space, each point represents a particular entity and a cluster of points represent an aggregate of entities. Entities can be processed with any manner of linear and nonlinear clustering, linear manifold clustering, and nonlinear manifold clustering in the embedding space where the clusters can have any dimension of N or less than N. The use of this embedded space to reduce dimensionality can provide more accurate health recommendations.

The adjudication process performed by the local adjudication modules 216 and 226, and global adjudication module 230 can monitor the clustering development as additional data sources and data types are added to and pruned from the clustering inputs. The local and global adjudication processes performed by the local adjudication modules 216 and 226, and global adjudication module 230 can further prune the linear, nonlinear, linear manifold, and/or NLM clustering that can lead to nonproductive regions of multidimensional spaces being eliminated from consideration for a particular health decision hyper-volume. In addition, these regions of the entity universe can be highlighted for future investigations by a domain expert. Feature vector tags can be preserved during the clustering process. Thus, the tags can allow the feature vectors to be traced back to their original information source through all processing modules. The clustering modules 212 and 222 can further perform manifold clustering, to replace Local Linear Embedding (LLE) and/or ISOMAP techniques (L-ISOMAP, C-ISOMAP, etc.), which can be vulnerable to metric error.

Dimensional weights and metric distance weights can be time dependent. For example, such time dependent dimensional weights and metric distance weights can be applied to gene mutations that occur over time, therapies, other types of mutations, etc. That is, selected dimensions can use time varying weights to move any combination of entities and/or clusters of entities closer to or further from one another, as a function of time and/or depending on the changing entity and/or varying attributes. Also, cluster formation and associated decision hyper-volumes can be a function of time. In at least one other, the attraction and/or repulsion between entities and/or centroids of clusters of entities can be controlled by the cost of a decision and/or a function of time.

The clustering modules 212 and 222 can use Monte Carlo insertion to initially place an entity into the entity universe and then use entity attraction/repulsion in the clustering processing to observe the trajectory of the placed entity. The system processor 128 can use Monte Carlo insertion of entities (one or more) to randomly place them into the entity universe and can use entity attraction/repulsion in the process and can use regular relaxation of prior entity insertions and to allow them to reach a positional equilibrium, that is where all forces are balanced, in the entity universe. The system processor 128 can place the entity into an entity universe based on Monte Carlo insertion with or without measure of importance. This process can continue until all entities have been inserted into the entity universe. The attraction and repulsion can impact the location of entities previously inserted into the entity universe. The entity-entity attraction or repulsion can be calculated by the system processor 128 based either on the similarity or dissimilarity of the entity-entity pair. In at least one other, the system processor 128 can directly insert the entity into the entity universe based on its attributes. If an entity is outside of any decision hyper-volume, it can be flagged for further investigation.

In at least one other, the clustering modules 212 and 222 can use Monte Carlo insertion with a measure of importance to place the entity into one or more selected hyper-volumes within the entity universe and then use the entity attraction/repulsion in the clustering processing to observe the trajectory of the placed entity until positional equilibrium is reached. The measure of importance for an entity can be used to select a hyper-volume, which contains the highest number of shared attributes and weighted attributes with the placed entity. This approach can reduce the amount of processing performed by the system processor 128 required for entity placement. Also, this embodiment can be used with seeding.

The linear, nonlinear, linear manifold, and/or nonlinear manifold clustering can be performed with the clustering modules 212 and 222 to form a set of local metrics for specific health science decision problems facilitating the use of many, tools and methods. In particular, weighted metrics and differential geometry can be utilized by the clustering modules 212 and 222 as one such tool to develop user recommendations. Other tools can include spectral theory and functional analysis.

The weighted metrics can indicate a formal metric and/or a pseudo metric. The formal metric can satisfy Euclidean geometry. The pseudo metric can approximately satisfy conditions for the metric since the decision solution can be a numerical result. The weight selection for the metric can be determined by the information content and/or importance of each entity. The weights can be determined during the process of solving the partial differential equation, as described, constructed, and illustrated below.

$\mathcal{F}$ can be a collection of finite length character strings, sequences or feature vectors (e.g., entities):

$$\mathcal{F} = \{A_j\} = \{A_1, A_2, \ldots A_M\}$$

$d_{ij}(A_i, A_j) = d_{ij}$ can be the metric on $\mathcal{F}$. A distance matrix can be formed as follows:

$$D(A_i, A_j) = [d_{ij}], \; i, \; j = 1, 2, \ldots M$$

This distance matrix is symmetric, zero diagonal, non-negative where:

$$S = \{\overrightarrow{a_j}\} = \{\overrightarrow{a_1}, \overrightarrow{a_2}, \ldots, \overrightarrow{a_M}\} \in \mathbb{R}^N$$

can be a (hypothetical) set of vectors having distance matrix D. Regarding the $\overrightarrow{a}_j$ as a field source, we can define a discrete scalar potential $\wp$ on S by:

$$\wp(\overrightarrow{a_i}) = g\Sigma_{j=1}^{M}\left(\left\|\overrightarrow{a_i} - \overrightarrow{a_j}\right\| - d_{ij}\right)^2 (*)$$

where $g$ can be a weighting or multiplier on affinity and is a non-negative constant that can be chosen arbitrarily to facilitate sensitivity analysis to determine a cost associated with a decision. The field can allow both the attraction and repulsion of entities in the field, and their positions/distances relative to one another, based on similarities and dissimilarities, respectively. The field can allow the non-linear manifold to be constructed and allow for measurement of metrics and subsequent determination of recommendation(s) and confidence regions. The field and its construction are described below.

In general, the existence of such an S for a given D is not guaranteed; in particular, D might not exist for N=1, but exist for N=2. Also, because S is informed only by the distances between the $\overrightarrow{a}_j$, any rigid placement of a solution is also a solution. Therefore, a solution can be registered in $\mathbb{R}^n$ for convenience. An approximate solution S for (*) can be found by various methods that include, for example, Singular Value Decomposition, Gradient Descent, and/or Monte-Carlo with or without the measure of importance.

A formal gradient:

$$\wp(\overrightarrow{a_i}) = C(\overrightarrow{a_i})$$

can define a vector field on, and that is precisely the set of zeros of the Laplacian of (which is to be expected). The field equations can give rise to a radially symmetric scalar potential that are used to drive the cluster formation. The cluster formation can be governed by entity data using the field equation. The closeness of entities and/or clusters of entities can provide recommendations for a given health science application. The details of this process are described below.

In addition, the linear and/or nonlinear clustering can be mapped (that is, embedded) onto at least one of linear manifold and nonlinear manifold with the clustering modules 212 and 222. The linear and/or nonlinear manifold distance or metric is the relative distance between feature vectors on the linear manifold and/or nonlinear manifold, respectively. The metric provides the relative affinity between feature vectors in the linear, nonlinear, linear manifold and/or nonlinear manifold spaces. The feature tags can then be used to reference the encoded feature vectors back to the source input and to follow the trajectory of selected entities within the entity universe. The reference metric can be used to indicate the affinity between the various entities described herein for the health science problem addressed.

A field can be defined as the sum of all attraction and repulsion forces of entities for each point in the entity universe. Each entity can have different attraction and repulsion forces in each dimension. Adding and/or subtracting entities to and/or from the entity universe can change or modify the field either locally (within a region) and/or globally (over an entire universe). Also, fields can be based on multidimensional feature vectors that can be arbitrarily defined. The field can consist of many dimensions and can change with time and/or with the addition (or deletion) of new (or existing) entities. The field can be classified as scalar, vector, tensor, statistical (many body), etc. Note, the method described of cluster formation using physical and/or mathematical constructs of attraction and repulsion can be controlled by the adjudication process described herein.

The "field" can govern the cluster formation used for generating the linear clustering, nonlinear clustering, linear manifold clustering, and/or nonlinear manifold clustering. The field controls the placement of entities (data from at least one database, including information of at least one entity with application specific databases and sensors metadata) into the linear, nonlinear, linear manifold and/or nonlinear manifold cluster formation. In addition, the placement of additional entities in an existing field can modify that field. The entities can both attract/repel other entities within the clustering process based on the defined field. The field can satisfy a superposition principle, so additional entities can be directly placed in the existing space. A health science decision hyper-volume can have a its own unique governing field based on contained entities. The field can be conservative. In particular, the field can be path-independent, not needing to retain the history to understand their immediate effect on the field. The entity universe and the interaction of all entities can be a mathematical construct that can be arbitrarily defined, including differing magnitudes, the fall-off or increase of force as a function of distance ($r$, $1/r$, $1/r^2$, or any other mathematical construct), time varying, no attraction/repulsion interaction between selected entities, or a combination of all three of these constructs. These force fields can be between entities or clusters of entities and/or combination of these. Different force fields can be applied to different entities and different multidimensional regions under the control of the local and global adjudication module 216, 226 and 230, respectively. Entities in the entity universe mathematical construct are not bound by physical constraints and can occupy the same position at the same time and move through other entities without disrupting the position of the entities until the positional equilibrium of the entity universe is reached (if so desired).

The resulting linear clustering, linear manifold clustering, nonlinear clustering, and/or non-linear manifold clustering, performed by the system processor 128, can be embedded in a Hilbert Space of appropriate dimension that creates coordinates in a natural way using unsupervised machine learning. The Delta Rule is a first-order gradient descent method. When the Delta Rule is written as a distance minimization expression, the Delta Rule can be a differential equation describing a vector field. A gradient descent solution (to place the data within a multidimensional coordinate space) can then be a set of Lagrangian Points (stable point or location within the multidimensional field where the forces are in equilibrium), which can satisfy this differential equation. In at least one other, the Hamiltonian formulation can be used. In this way, the field is an emergent property of the entity position, with the positions constrained by the mutual forces of attraction and repulsion. The dimension of the Euclidean Space can be selected by the system processor 128 to minimize error, and a machine-learning theory variant of the Delta Rule can be used to perform the clustering (of application specific metadata sensor and data, etc., and any combination thereof including subsets of the clusters). An energy function can be calculated from the solution of the differential equation. The energy function can provide a measure of how efficient/complete the clustering is to minimize the energy of the resulting field and allow the clustering to reach positional equilibrium. The formed cluster can correspond to a surface of minimum energy as defined by a partial differential equation of order 1 or greater. The concept of minimum energy ensures an optimum solution for a decision that can be achieved.

Other methods can be used to develop a distance matrix from the input data contained within the formed clusters, such as Singular Value Decomposition, Lagrange Multipliers, Newton's Method, or any other method that can construct a coordinate system from the data. In at least one embodiment, an adaptive convergence can be used where the attraction and repulsion is accentuated initially and then lessened as convergence of the cluster formation is reached to speed up the processing. In at least one embodiment, simulated annealing can be employed to halt the cluster formation processing after a fixed amount of time. The adaptive convergence and simulated annealing can be used in conjunction with each other. The adaptive convergence and simulated annealing can be performed in the math modules 214 and 224.

The system processor 128 can formulate and apply a weighted metric to entities. In at least one embodiment, this weighted metric can be a single weighted metric. The unification can allow the system processor 128 to uniformly treat entities in one or more dimensional spaces. From this single weighted metric, the system processor 128 can formulate an objective function which can drive the linear, linear manifold, non-linear, and non-linear manifold clustering. In this way, the cluster formation can be recursive, and adaptive (i.e., depending on the data). Other metrics can be created and applied to related data representations. For example, the system processor 128 can cluster entities. The objective function can be used to derive an Nth-order partial differential equation, for example, having the form of Laplace's Equation, the properties of which can characterize the linear, linear manifold, non-linear, and non-linear manifold clustering. In particular, properties of Laplace's Equation can allow data points, data dimensions, and data classifications to be added, removed, and modified without having to reconstruct the entire linear, linear manifold, non-linear, or nonlinear manifold clustering. The Laplace Equation, together with the use of weights in the metric, can be used by the system processor 128 to apply a unified representation to several operations without requiring data refactoring, such as:

1) clustering of entities including the interaction of previous health science recommendations;
2) clustering of health science entities data;
3) clustering of any combination and/or aggregation of entities data in the same, unified space; and
4) computation of numeric measures of vector distances or metrics between any and all of the above in the various unified spaces that can be used by the local 216 and 226 and global 230 adjudication modules.

The use of distances can include Euclidian, Riemann Manifold, other Nonlinear Manifold distances, etc.

The system processor 128 can divide entities into two more sub-entities. An entity can be divided into two or more sub-entities if the source information generating the feature vector for the entity is conflicting and/or sets the entity in a position that underlying information is negated or masked. At least one embodiment of this process can analyze the individual source term vectors, etc. for the entity and separate the entity into set of two or more sub-entities if the mean and/or variance (i.e., statistical moments) is above a threshold. Throughout this application, the use of the term sub-entity can be substituted for entity with regards to functionality. In at least one embodiment, the Monte Carlo technique, with or without the measure of importance, can be used to discover stable points for selected entities placed in the entity universe. Multiple entity stable points can be used to create the sub-entities. Stable points can exist where an entity and/or groups of entities are in positional equilibrium.

The clustering modules 212 and 222 can use an N-Dimensional visualization engine to compute and display descriptive statistics for the data, for example, minimum, maximum, range, standard deviation, mean, and/or histograms for entity population subsets. Automatic clustering (Autocluster Capability) may be selected to automatically group data into a domain expert-determined number of clusters based upon the relative distribution of data. The N-Dimensional visualization engine can be extensible by the addition of analytic tools such as a Feature Analyzer (Bayesian), Principal Component Analysis (PCA) (Karhunen-Loeve), and classifiers (e.g., Likelihood ratio, expert system, Radial Basis Function, Multi-Layer Perceptrons, rule inducers, etc.). Using a visualization process performed by the clustering modules 212 and 222 can allow for a domain expert to view the results of the linear, nonlinear, linear manifold and/or NLM cluster development in real-time or near real-time, allowing the domain expert to make adjustments or tuning the cluster formation process to test certain hypotheses. Visualization can be utilized for the training process.

The advanced analytics method 200, performed by the system processor 128, can generate an array of N-dimensional visualization engines that allow domain experts to view, manipulate, and analyze sets of discrete data points in high dimensionality, simultaneously. These visualization engines can make use of one or more of color encoding, position encoding, cluster and neighborhood encoding, and time encoding using frame-by-frame capturing of information in a video format, including virtual and/or augmented reality and/or sound encoding. Visualizing time and the clustering of disparate data in this way allows the viewing of the temporal formation, evolution, and disintegration of data features. Examples of this timing and clustering visualization can be mutation, aging, treatment therapeutic results, etc.

The advanced analytics method 200, performed by the system processor 128, can implement system commands that can allow selection of any number of sets or subsets of the data contained in Tables 1 through 9 by entities, sub-entities, attributes, and/or characteristics, in various manual approaches (Select Capability). A control device, such as a mouse and/or keyboard, can be used to select subsets of data right on the display device by enclosing them (e.g., Lasso Capability). Data subsets can be merged to create new subsets (Combine Capability); subsets can be disbanded (Clear Aggregates Capability). The domain expert can subsample the population (Sampling Capability) and mask out undesired data fields (Feature Projection Capability). These manipulations need only be done in early training and stored for future reference as domain expert preferences and/or workflows, after which the advanced analytics method 200 can be automated based on the stored domain expert preferences and/or workflows. These training techniques can be considered a subset of machine learning. The system controller 126 can be used to retrieve the data from any of Tables 1 through 9. Thereafter, the system processor 128 can use the retrieved data to generate an entity.

Data seeding can be performed during the clustering process performed by the clustering modules 212 and 222. Data seeding can force the multidimensional-clustering around designated regions of the multidimensional space (sometimes referred to herein as the hyper-volume). This seeding can highlight entities and/or clusters of entities with common attributes within a hyper-volume containing the seed. Known and/or conjectured diagnoses and treatments vectors, drug discovery, drug repurposing, etc. can be used for data seeding. The system processor 128 can identify an entity and/or cluster of entities containing a distinct set of attributes that are similar, that is close to the seeding attributes. Such data seeding together with multiple math models performed by the math model modules 214 and 224 and the adjudication process performed by the local adjudication modules 216 and 226 and global adjudication module 230 can highlight similar entities. Seeding forces the multidimensional-clustering around designated regions of interest. Note, the seed can be an entity that is defined by a user or the system processor 128.

In addition, seeding can be performed to direct cluster formation (defined subsequently) in certain locations within the multidimensional space. The seeding can be either weighted or unweighted. Similarly, masking can be used to filter entities from an existing cluster. Seeding can also be used in the adjudication process in conjunction with the math model modules 214 and 224 to measure confidence in the decisions (subsequently defined).

The math model modules 214 and 224 can perform predictive analysis, statistical analysis, statistical inference, and tracking on the conditioned data received from the data conditioning modules 210 and 220 or entities and/or feature vectors from the clustering modules 212 and 222 and/or in conjunction with the local adjudication modules 216 and 226 and global adjudication module 230. The mathematical model performed by the math model modules 214 and 224 can use multiple models to focus on the high pay-off regions within the linear, nonlinear, linear manifold and/or nonlinear manifold clustering processes. Output from each math model can be input into the adjudication process performed by the local adjudication modules 216 and 226 and the global adjudication module 230 and selected output can be used. The advanced analytics method 200 can use multiple models, including statistical models and deterministic models. These models can be applied to one or more of the embodiments disclosed.

Calculated with each statistical model is a confidence region or confidence interval. These models and confidence regions can be applied to all processing modules, e.g., data conditioning 210 and 220, clustering 212 and 222, local adjudication 216 and 226 and global adjudication 230. The calculations that can be performed in these math model modules 214 and 224 are disclosed as being used elsewhere in this application. Examples of these calculations include regression analysis, pattern recognition, Kalman Filtering, Maximum Likelihood Estimation, all statistical calculations, all metric distance and all angle calculations, and all vector and tensor operations.

Also, statistical analysis, statistical inference, prediction, tracking, change detection, detection and mathematical modeling can be performed in the math processor modules 214 and 224. Examples of these mathematical modeling can include statistical moments (centroids, means, variances, skewness, kurtosis, etc.), single and/or multiple linear and/or nonlinear regression, Maximum Likelihood Estimation (MLE), Bayesian calculations or any other mathematical modeling that allow for determination of recommendations and confidences, by the system processor 128. For the tracking of trajectories over time and/or the ingestion (deletion) of new (old) information, Autoregressive (AR) models, polynomial fit, splines, and Kalman Filtering, etc. can be utilized by the system processor 128, which can provide useful properties in a space and can compensate and/or predict changing, evolving and/or emerging patterns, sequences and/or structures in the data and/or metadata.

The mean of a cluster of entities or an aggregate and/or subset thereof can be represented by a centroid of that cluster in the N-dimensional attribute space (that is, the entity universe and/or a selected hyper-volume within the entity universe). For example, the centroid of a cluster of entities can be used to define a representative entity for that cluster.

The clustering modules 212 and 222 input selected data and output their results to the math model modules 214 and 224 to calculate applicable uniqueness measures, vector-space metric distances, inverse metric distances, cluster centroid and other cluster statistical moments, thresholds, term and feature vector weights and/or masks, metric distance weights, the minimization of a loss function, and the Bayesian decision quantities (e.g., likelihood functions, posterior predictive utility distribution of the vector x, and the expected loss (EL) under the predictive distribution). Note, the hyper-volume and associated boundary enclosing that hyper-volume can be calculated as well.

Using the techniques of information geometry, signature extraction, and building classifiers, etc., can be performed in the math model module 214 and 224.

Math models developed by the HSDP 100 can be used to identify and predict new relationships that can exist outside existing scientific knowledge and/or training datasets. For example, math models can identify and/or predict potential therapeutic dosages, efficacies, morbidities, mortalities and/or side-effects of new drugs, existing drugs, combinations of these drugs for certain patients and/or groups of patients. These models can be multi-scale (e.g., a DNA sequence, a gene, a cell, an organ and a human) and/or a function of time. These models can extend understanding of health science (e.g., drug discovery, disease diagnosis, disease treatment, species, and/or individual(s).)

The $L_k$ norm can measure the metric distance between any combination between entities and/or the centroid of entity clusters, etc. to establish decisions according to:

$$L_k(x, y) = \sum_{i=1}^{d} \left( \left\| x^i - y^i \right\|^k \right)^{1/k},$$

wherein x, $y \in R^d$, $k \in Z$
Where d is the number of dimensions in the entity universe.

In an example, $L_k$ norm with k smaller than 1 (that is, fractional) can be more effective at preserving the meaningfulness of metric distance in a high dimensional space. Many high dimensional algorithms use a Euclidian metric distance (k=2 defined below) as an extension to its traditional use in two-dimensions and three-dimensions. In at least one embodiment, the $L_k$ norm can be k=1 (Manhattan Metric Distance) or other values of k.

In other embodiments, the following metric distances can be used to determine a Pearson Correlation distance, Absolute Pearson correlation distance, Un-centered Correlation distance (same as Pearson Correlation distance with sample means set to zero), Absolute, Un-centered Correlation distance, and Kendall's (tau) distance (for nonparametric distance measurements).

Individual dimensions (i.e., attributes, weighted attributes, weighted combinations of attributes, masked attributes, etc.) within resultant linear, nonlinear, linear manifold and/or NLM clusters can be weighted to accentuate or diminish the importance of selected attributes. In addition, inter-cluster or inter-entity vector distances can be weighted to accentuate or diminish the relative sameness or difference of the clusters or entities. Furthermore, the NLM clustering process disclosed herein can increase the effective data signal-to-noise-ratio (DSNR) to improve detection of weak correlations between entities/attributes. The HSDP 100 can apply error minimization and linear, nonlinear, linear manifold and/or NLM cluster assignment techniques to achieve noise reduction. More specifically, these techniques will simultaneously and systematically minimize errors while maximizing the detection of health science recommendation in the clustering process and entity to cluster hyper-volume assignments.

The angular distance, "$A_k$," and the metric distance, $L_k(x, y)$, can be used in the adjudication process.

The angular measure, A, between two vectors, x and y (including a centroid(s)), in a high dimension vector space can be calculated using a normalized dot product of two vectors:

$$A_k = \cos^{-1}\left(x \cdot y / L_k(x, y)\right)$$

An entity can consist of data/metadata from Tables 1 through 9 or any combination (e.g., individual data, pharmaceutical data, publication data, genetic data, DNA, virus RNA, RNA, etc.). Some examples of metrics are a norm of a vector difference and a norm of a weighted vector difference. If required, the math model modules 214 and 224 can calculate all angles between multidimensional vectors between all entities or groups of entities.

A hyper-volume can be constructed within the entity universe (along a vector originating from an entity and/or centroid of a cluster of entities associated with a previous entity assignment (decision) to another entity and/or centroid of a cluster of entities using metrics and/or angles offset from that vector. This process can be repeatedly performed for each decision and used in the multistage iterative adjudication. This procedure can be used to include a new entity into an existing decision hyper-volume and can transfer the attributes of that hyper-volume to the new entity. In addition, the new entity can replace the cluster with a summation of the attraction and repulsion of all the entities in the cluster and the new entity can be used in the attraction and repulsion calculations instead of the individual entities in the cluster. This approach can radically simplify and speed up the attraction and repulsion processing.

The distance metrics and vector angles can be combined to calculate and track trajectories of entity, statistical moments, etc. (e.g., as a function of time) in the math modeling modules 214 and 224 under the control of the adjudication process performed by local adjudication 216 and 226. Regression analysis, Auto Regressive (AR), Auto Regression Moving Average (ARMA), Maximum Likelihood Estimation, or Kalman Filtering can be used to predict and track this trajectory, and predict changes to decision boundaries. The use of these techniques can detect the number of entities/attributes and/or the rate of change of entities/attributes as a function of time for individuals, diseases, symptoms, diagnoses, treatments or any other attribute contained in the tables. Subsequent processing iterations can be selected and controlled by the local and global adjudication processing modules 216, 226, and 230 based on rules and associated actions and based on the output from the math model modules 214 and 224.

The math model modules 214 and 224 can use a covariance matric to construct confidence regions and sensitivities. This sensitivity matrix can be used to model the sensitivity of quantities to variations in parameters (e.g., time). Many math modeling methods (e.g., regression, AR, MLE, Kalman Filtering, etc.) are available for use with the disclosed embodiments.

Adjudication can be performed using the local (intra-branch) adjudication modules 216 and 226 and/or the global (inter-branch) adjudication module 230. For clarity in further discussions, a branch refers to a single set of processing modules 206 and 208 with the local adjudication module 216 operating only with modules 210 to 214 and inter-branch refers to operating across all branch processing chains in which the global adjudication module 230 interacts with the local adjudication modules 216 and 226. This two-stage adjudication is discussed for simplicity. In at least one embodiment, multistage adjudication can include any number of stages and any feed forward and/or feedback stage interconnections. The various interconnects illustrated in FIG. 2 can be bi-directional. And, in an example at least one or more global adjudication modules 230 can exist and connect to a super global adjudication module (not shown).

Multistage adjudication control can include (1) control of processing retrieved and/or entity flow and routing among branch modules 206 and 208 and across branch modules 206 and 208, (2) control of algorithm selection and associated processing parameters in branch modules (e.g., type of clustering, dimension reduction techniques, etc.), and/or (3) control of a number of iterations through given branch modules based on the risk function (subsequently defined), cost function (defined subsequently), error and/or the expected loss (subsequently defined), which can minimize the risk and/or cost of a wrong recommendation being made and/or minimize the risk/cost of a valid recommendation not being made.

The local adjudication modules 216 and 226 can select decision cost functions (e.g. quadratic, absolute value, etc.).

This decision cost function can be used to measure elasticity and/or sensitivity in the decision process. For example, in the health sciences, the decision cost function can be a decision cost to a pharmaceutical company, a patient, a government, and an insurance company, a therapeutic dosage, a patient response, a patient side effect, a patient morbidity, a patient mortality, etc., or a combination of these.

The advanced analytics method 200 can use an adjudication process performed by the local adjudication modules 216 and 226 to systematically select the best decisions (e.g., minimizing loss/cost/error) produced by branch modules 206 and 208 for a given entity. The adjudication process, performed by the local adjudication modules 216 and 226, allows the objective and principled application of mathematics and knowledge to render a summary assessment by fusing information from Tables 1 through 9 and produce reports giving insight into the reasoning system behind the system processor 128 conclusions.

The global adjudicator 230 can use branch decisions, and apply principled analytic techniques and knowledge to produce a fused product that is generally "better" than any of the single branch decision alone (subsequently defined). Decisions can be used to discover relations, processes, events and/or highlight overt and obscure structures, patterns and information using principled analytic techniques, as well as prediction and confidence region using cluster parameters, decision regions (hyper-volumes and boundaries) and/or entity assignments.

Iterations can be performed and compared in the adjudication modules 216 and 226 for use in pruning of nonproductive data, nonproductive processing branches, math module computations, etc. Local adjudication 216 and 226 can use a set of rules, as examples, to control the selection and masking of source data, data conditioning, cluster formation, math models, and adjudication methods, etc. throughout the branch processing. The global adjudication module 230 can also feedback control and data via the bidirectional global adjudication feedback bus 244 and 254 function in which results and control are fed back to the previous local adjudication modules 216 and 226. The local adjudication modules 216 and 226 can also control feedback functions in which results (e.g. metadata, results, etc.) can be fed back to prior processing modules. The local adjudication modules 216 and 226 can feedback control and data via the local adjudication feedback bus 242 and 252 to the data conditioning modules 210 and 220, the clustering modules 212 and 222, the math model modules 214 and 224, respectively.

A decision boundary can be a threshold, a multidimensional surface enclosing a decision/discovery region or multidimensional hyper-volume. The surface can be defined as containing the hyper-volume, that can include a null set(s), an entity or groups of entities and/or entity clusters, that separates that hyper-volume from the remaining entity universe. All relevant entities and entity clusters can be defined by a set of attributes, including weighted attributes, combinations of weighted attributes, masked attributes, etc. Recommendations can be generated in the system processor 128 and transmitted from the system controller 126 to a UE 110 for presentation to a user, such as via a local display, a web interface, augmented/virtual reality, and/or any other human-computer interface.

The adjudication performed by the system processor 128 can include statistical decisions, neural network processing, or a combination of these. The system processor 128 can generate decisions/reasoning that can be presented to the user in a rank ordered list based on a confidence region. Information can be combined in two or more entities by forming a derived entity by combining the attributes. The derived entity can be then processed as a standard entity.

The system processor 128 can make optimal decisions under uncertainty of outcomes using statistical decisions. One way of addressing uncertainty can use probabilistic and statistical reasoning. A common method of this is Bayesian decisions coupled with expected utility maximization, discussed herein. Decision systems have been developed for various applications. These systems can be passive vs. active, individual vs. collaborative, non-Bayesian vs. Bayesian, and Parametric Bayesian vs. Non-Parametric Bayesian. All of these systems or combination thereof (called hybrid filtering) can be used with the system processor 128 described herein.

The system processor 128 can balance two types of errors. Type I error is a false positive. Type II error is a false negative. A decision threshold can be established to balance Type I and Type II errors using a decision cost function. Examples of cost functions can include monetary, drug dosages, drug side effects, drug efficacy, diagnoses, treatments, drug active ingredients etc. (or combinations thereof) for health sciences. The calculation of Type I and Type II errors can be performed in the math processing modules 214 and 224 and the balancing of the Type I and II errors can be under the control of the adjudication modules 216, 226 and 230. Type III error is a result of making the correct decision for the wrong question. Note, if required, the system processor 128 can use other higher order error types. Note, in medical and biological sciences the terms sensitivity, that is, the true positive rate or the probability of detection, and specificity, that is, the true negative rate, can be used. Sensitivity can quantify avoiding false negatives and specificity can quantify avoiding false positives. Therefore, the system processor 128 can present error types in user jargon for greater understanding.

The system processor 128 can make statistical decisions that can be used to manage uncertainty by minimizing the expected loss and/or cost of a wrong decision, for example, wrong diagnosis, wrong treatment, a promising new drug that fails an FDA phase testing, and the failure to understand and prevent adverse drug-drug interactions. At least one embodiment can use a Maximum Likelihood Estimator. Also, embodiments can use at least one of different probability distributions, for example, Gaussian, Uniform, Binomial, Poisson, Exponential, and any other probability density functions that can provide for managed uncertainty.

A loss function can be used to minimize the cost, risk and/or error of decisions. Examples of loss functions are regret, quadratic, 0-1, absolute value, etc. In the case where the loss function is a random variable, Frequentist and Bayesian expected loss can be calculated. In at least one embodiment described herein, Bayesian expected loss (expected loss and EL(x) are used interchangeably with Bayesian expected loss herein) can be calculated using the loss function l(x,u). The expected loss can also be used to minimize the cost, risk and/or error of decisions. Note, vectors are represented by bold characters. Bayesian decisions use the following definitions: the utility function, u, can be defined by 1) a probability model parameter space M (the probability model can be locally selected), 2) observation data D, 3) an initial or iterative processing pass specified prior p(M) over the model parameter space M and 4) an initial or iterative processing pass probability model p(u|x, M), and can update the posterior over M using Bayes' rule:

$$p(M \mid D) = [p(D \mid M)p(M)]/p(D)$$

Where p(D|M) is called the likelihood function. The posterior predictive utility distribution of the vector x is:

$$P(u \mid x, D) = \int_M p(u \mid x, M)P(M \mid D)dM$$

In order for the system processor 128 to determine the optimal decision, that is, the best decision, Bayesian decisions can utilize the loss function, which is an overall measure of loss/cost/risk/error incurred in taking any of the available decisions or actions. This loss function, l(x,u), can be defined as the loss incurred by recommending item x when the true utility function is u. Then the Bayesian expected loss for deciding x is defined for both Type I and Type II errors as the expected loss, EL(x), under the predictive distribution given by:

$$EL(x) = \int_u l(x, u)p(u \mid x, D)du$$

The expected loss can be used in both the local adjudication 216 and 226 and global adjudication 230. The risk function can combine the loss function l(x,u), rules, actions, and the probabilities. More precisely, the risk of a decision is the expected loss with respect to the probabilities p(u|x, D). Other loss function embodiments such as a quadratic loss, squared loss, absolute value loss, etc. can also be used. The quadratic loss function can be used in t-tests, regression models and other statistical methods.

Note: if x is made up of discrete values (instead of continuous values) then the integral can be replaced by a summation. Also, a multi-attribute utility function, u(x), can be defined over a vector x with n dimensions, $\{x_1, \ldots, x_n\}$ using $u(x)=u(x_1, \ldots, x_n)$.

For Bayesian decisions, the optimal item x* that minimizes the expected loss:

$$X^* = \arg\min EL(x), x \in X$$

The x can be used to define the decision boundary(ies) between entities and entity clusters in the multidimensional entity universe.

The expected loss and/or cost for both Type I and Type II errors can be weighted. The weighting can represent the relative loss/cost/risk/error of each type of error (Type I and Type II) and can change the decision boundary/threshold.

This equation represents an optimization with the local adjudication 216 and 226, where an absolute optimum (in this case, the minimum) is determined over all x∈ X in each processing branch as shown in FIG. 2. Bayesian optimization can maintain a probabilistic belief and/or disbelief about the expected loss (EL) and based on an acquisition function to determine where to evaluate the function next. Optimization methods are subsequently discussed herein.

The x* represents the decisions presented to the user together with a decision score that can indicate a likelihood that decision is correct. The decision score can be 1) based on the decision confidence (defined subsequently), 2) scaled and/or 3) can work with linear, logarithmic, and/or other compressive scaling techniques. In at least one embodiment, the decision can also be represented by a number of symbols, and/or any other quantitative symbolic representation of accuracy.

The system processor 128 can use many acquisition functions that can be interpreted in the framework of Bayesian decisions, such as evaluating an expected loss, EL(x) at a given point x. This evaluation can produce suboptimal results when the entire entity universe is considered, but an optimal result can exist for a selected multidimensional subregion of the entity universe. For some applications, like precision medicine, such as coordinated drug use and therapeutic drug dosages for an individual, etc., then the suboptimal solution can be the better decision for a particular individual, treatment, etc. Other embodiments of the acquisition function can include Probability of Improvement, Expected Improvement, Entropy Search and Upper Confidence Bound, etc. For simplicity of explanation, the acquisition function can evaluate the expected loss, EL(x) at a given point x.

The system processor 128 can select the retrieved dataset to ensure an optimum decision. In at least one embodiment, the entity can be weighted and processing methods can be combined to improve the decision process. The adjudication process performed by the local 216 and 226 and global 230 adjudication modules can select optimized weights for the term and feature vectors and weighted metric distances.

An example embodiment of the interaction between the entity selection and processing modules is present here. The local adjudication modules 216 and 226 can observe the output of the math model modules 214 and 224 for a given set of formulated data and a given set of processing methods, i.e., the data conditioning modules 210 and 220, and clustering modules 212 and 222. This output can include a uniqueness measure, that is an identification of an entity and/or cluster of entities containing a distinct set of same or similar attributes, metric distances, metric distance statistics, and cluster statistics while the adjudication modules 216 and 226 monitor the expected loss. In addition, effects of thresholds/region settings, feature vector and feature vector weights, metric distance weights, and the calculation of the Bayesian decision quantities, for example, the likelihood function, posterior predictive utility distribution of the vector x, can be performed while monitoring the EL(x). The EL(x) can also be used in dimensionality reduction, e.g., reduce the number of attributes, combined attributes, weighted and combined attributes, etc. The local adjudication modules 216 and 226 can include a set of rules and associated actions, and can initiate each of the methods of data conditioning modules 210 and 220, clustering modules 212 and 222, and math processing modules 214 and 224 to minimize the EL(x).

Optimization can be used to find arguments of an EL(x) function which can yield its minimum, that is, looks for a global minimum of the objective function. Note, optimization can minimize the EL(x) objective function and/or maximize the negative of the EL(x) objective function (e.g. reward, etc.). For machine learning cost, EL(x), and/or error objective functions are typically minimized. Such optimization can be performed using numerically, e.g., which can involve guessing, or analytically, e.g., which can involve computing derivatives of the objective function and looking for critical points. This process can continue until the global minimum, i.e., the minimum for the entire objective function, is found. Note, these methods can be performed on multidimensional objective functions.

Optimization can be divided into Convex, that is, without saddle points, and Constrained, that is, optimized over a region and/or set of feasible point. Example of constrained optimization is the Karush-Kuhn-Tucker method using generalized Lagrangian, Gradient verses Non-gradient methods, Gradient Descent, Stochastic Gradient Descent, Simulated Annealing, Nelder-Mead (Simplex or Amoeba), Particle Swarm, Evolutionary Algorithms (Genetic Algorithms, Evolutionary Strategies, Evolutionary Programming), Derivative-Free Optimization, Hessian Optimization, Advanced Algorithms (Conjugate Gradient, BFGS, L-BFGF), etc. Examples of optimization of multidimensional objective functions can also be used with TF.IDF for dimensionality reduction and clustering formation.

The minimum loss function and/or expected loss can be calculated to find the decision boundary and/or boundaries for the selected hyper-volume containing a group of and/or cluster of entities. The gradient decent method can be used to find the optimum decision boundary. This multidimensional decision boundary can be used to select the data, select module processing methods and control the processing for each module or group of modules to minimize the expected loss. The adjudication can minimize a loss function (e.g., expected loss) associated with the optimal assignment of the entity from the multidimensional clustering by adjusting a multidimensional decision boundary of the multidimensional decision hyper-volume.

Uncertainty can exist in any health science recommendation process that resides in the system processor 128. There can be multiple embodiments to manage uncertainty and system reasoning. These embodiments can include statistical reasoning, constraint solvers, logic programs, rules engines, deductive classifiers, machine learning systems, case-based reasoning systems, and procedural reasoning systems. In at least one embodiment, the system processor 128 can minimize the Root Mean Square Error (RMSE) across all decision hyper-volume to set threshold and/or boundaries. In at least one embodiment, the system processor 128 can minimize the Root Sum Square Error (RSSE) across all decision hyper-volume to set threshold and/or boundaries using linear and/or nonlinear regression analysis. In at least one embodiment, the classification can be rule-based systems which are based on selected axiomatic rules, that is, unquestionable rules, such as the standard of care as defined by CMS Quality Measure Benchmarks.

The selection of clustering, e.g., linear, nonlinear, linear manifold and nonlinear manifold, methods performed by the system processor 128 and the metric distance statistics and the cluster statistics can be used to determine the similarities and distinctions between entities, clusters of entities and/or a combination of these. The smaller the metric distance is, the greater the affinity or similarity between entities. Correspondingly, the larger the metric distance is, the greater the differences between the entities. In at least one embodiment, the system processor 128 can use the closeness of one entity to another entity to transfer a decision, in whole or in part, to the second entity. In at least one embodiment, multiple decisions thresholds and/or boundaries can be set based on the inverse distance, or inverse metric, and/or the distance, or metric, between an entity cluster centroid, or a defined location in the entity universe, and another entity or entity cluster. Using the metric, closeness can be defined if the metric is less than a threshold. In another example, using the inverse metric, closeness can be defined if the inverse metric is greater than or equal to a threshold. The example embodiment described hereafter uses the inverse metric exceeding, or crossing, a threshold and/or boundary as a basis for determining a decision. In at least one embodiment, multiple decisions thresholds and/or boundaries can be set based on combination or the inverse distance and the angular measure (previously defined) between an entity cluster centroid, or a defined location in the entity universe, and an entity or entity cluster. Using a combination of inverse metric and angular measure, closeness can be defined if the combination is less than a threshold.

Individual entity thresholds and/or boundaries can be optimized using the information contained in health science Prior Run Archive, using machine learning and based on the probability and cost of a missed recommendation, that is, missing the opportunity to take an action, and the probability and cost of an erroneous recommendation, that is, providing misinformation. In at least one embodiment, single and/or multiple linear and/or nonlinear regression, Maximum Likelihood Estimation (MLE) calculations can be used for decisions. The local adjudication modules 216 and 226, and global adjudication module 230 can perform an adjudication process that can establish thresholds and/or boundaries and decisions when these thresholds and/or boundaries are crossed.

In at least one embodiment, the local and global adjudication modules 216, 226, and 230 using Bayesian decision theory can be extended to a game theoretic approach using decision cost. This approach can use knowledge of decision cost of the entities and/or clusters of entities to modify decisions. Bayesian decisions can be formulated for decisions for individual entities and/or clusters of entities. Game theory can be used to formula an optimum decision cost strategy and can build on the intra-branch and inter-branch adjudication multistage structure, previously described.

In at least one embodiment, the local and global adjudication modules 216, 226, and 230 can be implemented using a neural network. Neural network weights, biases, and thresholds can be manually and/or automatically controlled by the local adjudication modules 216 and 226 and the global adjudication module 230. The local adjudication modules 216 and 226 and the global adjudication module 230 can learn and/or train using a training set (subsequently discussed). Various types of neural nodes can be used with the local and global adjudication modules 216, 226 and 230. These nodes include perceptron and the sigmoid neurons, learning/training algorithms, e.g., stochastic gradient decent, recurrent neural networks, multi-layer feed forward network and the multi-layer feedback network, Radical Bias Functions (RBF), Recurrent Neural Networks (RNN), Hopfield Network, Boltzmann Machine, Self-organizing map, Learning vector quantization, Echo State Network (ESN), long short-tern memory network, Bidirectional RNN, Stochastic Neural Network, and many Modular Neural network which can include Committee of Machines, and Associative Neural Network.

Cost functions can be incorporated into neural networks and can be similar to the utility function associated with Bayesian decisions discussed herein. For example, the cost function, C, can be the quadratic cost function. This cost function can indicate how good the training is. The aim of training is to minimize the cost function C varying a set of weights and biases using gradient decent method (subsequently defined). Other cost functions can include Cross-Entropy cost, aka, Bernoulli negative log—likelihood and Binary Cross-Entropy, Exponential cost, Hellinger distance, Kullback-Leibler divergence, and Itakura-Saito distance. The use of the cost minimization can measure the effectiveness of the neural network implementation, that is, weights and biases, in solving the decision problem like the statistical decision approach presented previously.

The global adjudication module 230, in conjunction with the local adjudication modules 216 and 226, can perform adjudication that can allow the strength of one component of the decision process to compensate for weaknesses of another process (subsequently defined). The methods of statistical decisions and/or neural networks can be used to perform this multistage adjudication. For simplicity, statistical decisions and neural networks are discussed independently. However, in at least one embodiment both approaches can be applied synergistically in multistage adjudication for decisions in the same adjudication module and/or different adjudication modules. A result of such adjudication allows for optimized use of an available entity, information, processing, and associate processing parameters. And, the local 216 and 226 and global 230 adjudication modules can construct an optimized processing solution for a given health science problem and associated retrieved and/or the entity by principled selection and control of these datasets and local/global adjudication modules 216, 226, and 230. Additionally, methodology of data selection and data conditioning utilized by the system processor 128 can differ depending on the retrieved and/or the entity used and the math processing modules 214 and 224 modeling used in conjunction with the type of clustering used.

After the expected loss has been minimized by the system processor 128 for each processing branch established by the local adjudication modules 216 and 226, the results from each processing branch can be input into the global adjudication module 230. The global adjudication module 230 can combine one or more processing branches and the entity to create a fused solution for the system processor 128 on an entity-by-entity basis. The global adjudication module 230 can select and control different processing techniques in various regions of the multidimensional decision hyper-volume. The global adjudication module 230 can direct each local adjudication module 216 and 226 using a unique set of rules to guide and find the global optimum, e.g., gradient descent. This minimization of posterior predictive utility distribution of the vector x can be iterative and performed until an optimized $X^*$ is found and can create an ordered list of decisions and associated decision scores provided to the user device together with the reason for each decision. This list can be transmitted to the UE 110 by the system controller 126. In at least one embodiment, the local and global adjudication modules 216, 226, and 230 can use statistical decisions, neural networks and/or combination of these methods to select retrieved and/or the entity, select and control branch processing modules, and control processing flow to provide a decision. Statistical decisions and neural networks can be used synergistically using the system processor 128 architecture herein disclosed.

Creating an optimum decision boundary can be defined as follows: 1) Create multidimensional cluster of entities/sub-entities based on attributes and feature vectors using at least one of many linear, linear manifold, nonlinear and nonlinear manifold clustering methods, 2) use at least one of Bayesian Decision and neural network processing to calculate a multidimensional decision hyper-volume and associated decision boundary for each type of clustering to achieve a minimum EL(x) using gradient descent to assign entities (sub-entities) to decision hyper-volumes, and 3) global adjudication can select the lowest expected loss across the clustering methods used as the solution.

In at least one embodiment, the system processor 128 can use the minimum expected loss solution and can assign individual entities to a given decision hyper-volume using the highest decision confidence from each clustering method used. Each entity decision confidence can be calculated based on cluster statistics and/or decision boundaries enclosing said entity and/or cluster of entities, reaches positional equilibrium, or a combination thereof. For precision medicine applications, e.g., individuals, diagnostics, treatments, diseases, etc., this approach can improve results for a specific entity, such as a person.

In at least one embodiment, the entity cluster centroids and number of clusters from the selected lowest expected loss adjudication can be used for seeding other non-selected clustering methods to re-perform each non-selected clustering method. The number of clusters can be limited to the same as the selected lowest expected loss method. The individual entities can then be assigned to a given decision hyper-volume using the highest decision confidence from each clustering method used. In at least one embodiment, the entity cluster centroids, such as location and number, from the selected lowest expected loss adjudication (defined previously) can be used for seeding the other non-selected clustering methods to re-perform each non-selected clustering method. The number of clusters within the entity universe can be limited to the same as the selected lowest expected loss method. The individual entities can then be assigned to a given decision hyper-volume by performing a weighted sum derived from each clustering method. The weighting is based on the decision confidence from each respective clustering method.

Any of the decision and/or entity assignment embodiments can be applied regionally to adjacent decision hyper-volumes sharing a decision boundary(ies). The entity regional universe can use weighted regional optimum entity assignment(s) to produce a regionally more precise decision boundary(ies) for an entity and/or group of entities. Note, this approach can allow more accurate decisions necessary for precision medicine (e.g., patients. diagnoses, treatments, etc.). Note, here the posterior predictive utility distribution of the vector x can be minimized for the selected hyper-volume and the enclosed entities. Although the vector x may optimize the loss function to set decision boundaries across the entity universe, the vector x can be optimized locally within a selected region or selected hyper-volumes. Therefore, each selected hyper-volume and/or groups of hyper-volumes in the entity universe can be optimized independently. This can be useful for precision medicine applications. The approach described here can also reduce the required samples and/or convergence time for training for a given decision hyper-volume. Note: a separate decision hyper-volume can also exist within a larger hyper-volume. The ability to separate hyper-volumes within larger hyper-volumes is critical to identify and/or differentiate diseases, conditions, and treatments that can also exist within the larger hyper-volume. Decision hyper-volumes can be either overlapping and partially overlapping hyper-volumes.

The system processor 128 can perform any of the embodiments iteratively and can be performed until the optimum entity assignment is achieved. Successive iterations can select the data flow and processing control until the minimum expected loss can be achieved and the optimum assignment of the entity close to a given boundary can be made. Also, the global adjudication module 230 can select the best embodiment and/or combinations of embodiments that optimizes entity assignments (e.g., near a boundary) and minimizes the expected loss for the regional minimization and/or global minimization of posterior predictive utility distribution of the vector x. The global adjudication module 230 can also determine the weighting of results from the different intra-branch processing embodiments and/or combinations of these. For example, the system processor 128 can make health science recommendations, such as the best treatment for disease and/or combinations of diseases, the best drug and/or combination of drugs to treat a given disease and/or combination of diseases for a given individual which can minimize side-effects and enhance treatment, and/or any combination of problems in Table 1 through 9.

The multistage adjudication performed by the adjudication module(s) 216, 226, and 230 can be trained. The adjudication module(s) 216, 226, and 230 can perform two methods of training learning machines: unsupervised and supervised. Unsupervised training can exclude known results during training. Input data can be grouped (e.g., exclusively) on the basis of its statistical properties and clustering. Supervised training includes both the training data and the desired outcome data. The use of seeding in the case of supervised training can improve the accuracy of the clustering, potentially reduce the size of the training data set, and can control the bias in the clustering process. The construction of a proper training set can maximize decision accuracy, reduce the training set, and minimize selected set bias. A proper training set can be constructed using known results, e.g., individual, disease, treatment, etc., and/or reserving a portion of the data for training and then using the results of this training set to process the remaining data. The approach described here can also reduce the required supervised training samples and/or convergence time for unsupervised training for a given decision.

The system processor 128 training can use an iterative, multi-mode, math model. Multiple views of the data space can enter a trainer, typically located in the local adjudicator 216 and 226, which can use an adaptive algorithm to infer modeling parameters. These constitute a collection of candidate solutions to the modeling problem which are assessed and calibrated to create a hybrid system for performing adjudication. Results that are ambiguous or have an inconclusive decision assignment can be used to identify areas for further investigation of undiagnosed diseases, new and repurposed drugs and/or combinations of drugs, etc. At least one embodiment can use Artificial Intelligence (AI) methods in hierarchal adjudication process. AI can be performed by one or more neural networks, statistical methods, and/or computational intelligence.

TABLE 10

| Functional Process Flow | |
|---|---|
| Process | Description |
| 1 | Select and preprocess data - On subsequent iteration passes, the adjudication controls the selection of data and data preprocessing techniques |

TABLE 10-continued

Functional Process Flow

| Process | Description |
|---|---|
| 2 | The text processing can generate the term vectors from the using Information Theoretic (e.g., TF.IDF), and can perform Syntactic and Semantic processing techniques associated with any and/or all input textual data selected and processed in process 1. |
| 3 | Feature vectors can be generated by summing weighted term vectors from operation 2 and appending additional information that is outside text processing. The feature vectors can then be tagged. |
| 4 | Term, intermediate, and feature vector dimensionality reduction can be controlled by utilizing information loss/gain in the PCA, SVD, and/or SVM processing. The dimensionality reductions can also be controlled by using the Expected Loss and/or mutual information. |
| 5 | Generate entity universe axes by combining term feature vectors and feature vectors attributes. At this point all dimensions/unit vectors for the health science application can represent the entity universe (that is, span the multidimensional space).<br>The feature vectors calculated in operation 4 represents the "entity universe" in which data from Tables 1-8 can be incorporated. |
| 6 | The clustering process can use any form of linear, nonlinear clustering, or linear manifold, as well as nonlinear manifold clustering. |
| 7 | Data Seeding can be used in the clustering process and/or the adjudication process. |
| 8 | Monte Carlo insertion using entity attraction/repulsion can be used in the clustering process with relaxation. Also, the system processor 128 can directly insert the entity into the decision hyper-volume based on its attributes |
| 9 | The system processor can divide entities into sub-entities and reperform the clustering. |
| 10 | Math Processing can calculate metric distances and associated statistical moments, detect changes in the entity universe and prediction. The metric distances of entities (or cluster of entities) to other entities and/or clusters of entities. This can include different $L_K$ norm formulations and the angular A "distance", as well as other functions.<br>In at least one embodiment, metrics can use the processing where the system processor 128 highlights an entity, a set of entities (or combination of sets of entities). |
| 11 | Adjudication to control processing: Multistage adjudication control can include (1) control of processing selected retrieved and/or the entity flow and routing among intra-branch processing modules and inter-branch processing modules, and (2) control of algorithm selection and associated processing parameters in all processing modules and/or groups of processing modules as previously defined, and (3) control of a number of iterations through a given processing modules and/or groups of processing modules based on the risk/cost/loss function, cost function, minimizing the decision RMSE and/or RSSE, and/or the expected loss, which can minimize the risk and/or cost of a wrong recommendation and/or minimize the risk/cost of a valid recommendation not being made. Further description of this process is defined in Table 11.<br>The methods of reasoning, including statistical decisions theory and/or neural networks can be used to perform adjudication. Both approaches can be applied independently and/or synergistically in multistage adjudication for decisions in the same adjudication module and/or different adjudication modules.<br>The adjudication process can be done in parallel or in iterative runs. |

Table 10 can include an example functional process flow for the system processor 128 implementing the various modules illustrated in FIG. 2, as discussed throughout this disclosure. In Table 11 Adjudication and Optimization implementation can use a Bayesian approach, and the role of the domain expert can be defined. Table 11 is included in Table 10, process 15. For example, Table 11 can include example Bayesian adjudication, optimization, and training. Initially, the domain expert can select the HSDP 100 for a particular health science application, the retrieved datasets, the size of the retrieved and/or the entity, the training method, processing methods, loss/cost/risk choice, entity assignment method and training methodology. The HSDP 100 can perform the iterations, decision boundary development, entity assignments and selects the minimum expected loss for the entity universe. The HSDP 100 can be used to build biologically-relevant models by the domain expert. Therefore, the HSDP 100 can become an experimental platform to test hypotheses, for example, drug efficacy, disease causation, etc. In at least one embodiment, Table 11 Adjudication and Optimization implementation using neural network can be defined, and the role of the domain expert can be defined.

In at least one embodiment, Table 11 Adjudication and Optimization implementation can use one or more Bayesian and/or the neural network approaches for different regions within the solution space, i.e., the entity universe, and the role of the domain expert can be defined.

TABLE 11

| Bayesian Adjudication, Optimization, and Training | |
|---|---|
| Process | Description |
| 1 | System processor can select data/metadata from one or more Tables. A manageable subset of data/metadata or limited dimensionality (masking) can be used based on initial conditions. |
| 2 | Perform parallel process on same selected data/metadata using different algorithms in each processing module (e.g., different data and data conditioning, different clustering methods, different math models, etc.). This can be done selectively. |
| 3 | Select best combinations or regional segmented combinations from process 2 methods using the expected loss. (Other methods (e.g., MLE, Kalman Filter, Minimize RMSE, Minimize RSSE, entropy, etc. can be used) |
| 4 | Modify cost function equations for the expected loss to set optimum threshold(s) and regions.<br>Observe result of changes using the expected loss. Optimum processing strategy minimizes expected loss. For the processing module under test |
| 5 | Based on the expected loss and associated utility function and entity/ attribute vector freeze the methods in the module under test and vary other modules at least one other module and observe the change in the expected loss. |
| 6 | Use global adjudication to select best processing branch. Repeat processes 1 to 5 as required continuing to observe the expect loss processing performed in the math model module |
| 7 | Rate of convergence/divergence, determination of cluster inclusion, bias, etc. as a tool to signal off ramp |
| 8 | Domain Expert can control training process, initial data set and dimensionality, maximum data set and dimensionality, method of expansion of data set and dimensionality, class of cost functions (e.g. cubic, quadratic, etc.), update coefficients for cost functions, thresholds, bias of data, weights and masking, collaborative filtering, etc. |

FIG. 3 illustrates an example system processor 128, in accordance with one or more possible embodiments. The system processor 128 can be configured as an array of computation units with computation units 1-A thru T-A making up a first column of computation units, computation units 1-B thru T-B making up a second column of computation units, computation units 1-C thru T-C making up a third column of computation units, and computation units 1-S thru T-S making up the Sth column of computation units. Computation units 1-A, 1-B, 1-C, and 1-S can make up a first row of computation units, computation units 2-A, 2-B, 2-C, and 2-S can make up a second row of computation units, computation units 3-A, 3-B, 3-C, and 3-S can make up a third row of computation units, and computation units T-A, T-B, T-C, and T-S can make up an Sth row of computation units. The system processor 128 can include, for an example, six horizontal high-speed switches 310, 312, 314, and 316 and, for example, five vertical high-speed switches 320, 322, 324, 326, and 328. The high-speed switches 310, 312, 314, 316, 320, 322, 324, 326, and 328 can facilitate rapid reconfiguration of the array of computation units 1-A thru T-S. This design is data-driven, highly parallel and highly scalable. This disclosure describes the architecture and processing performed in the system processor 128, together with a description of each processing blocks and its interaction with all other processing blocks, as well as the implementation and operation of the recommendation making performed in the system processor 128. A grouping of a set of computational units can form a computational unit from the computational unit 1-A thru 1-S. Although the example system processor 128 is illustrated as being a T by 4 processor array, the system processor 128 can be any configuration of any number of processing blocks within rows and columns that optimizes the processing of algorithms discussed herein. All interconnects shown in FIG. 3 can be bi-directional.

FIG. 3 illustrates a parallel implantation of the system processor 128. In at least one embodiment, all calculation can be performed serially and interim calculation results can be stored for use in subsequent operations. The system processor 128 can include a parallel multi-branch architecture that includes vertical crossbar switches 320, 322, 324, 326, and 328. These switches can be controlled via a set of rules from at least one or more local adjudication modules 216 and 226 and at least one or more global adjudication modules 230 in the multi-branch parallel architecture shown. All input information or prior run archives may exist in databases and be input to the system processor 128 and can be stored in the system processor storage 340.

It should be understood that, notwithstanding the particular operations as shown and described in the figures, a variety of additional or different operations can be performed depending upon the embodiment, and one or more of the particular operations can be rearranged, repeated or eliminated entirely depending upon the embodiment. Also, some of the operations performed can be repeated on an ongoing or continuous basis simultaneously while other operations are performed. Furthermore, different operations can be performed by different processing blocks or in a single processing block of the disclosed embodiments. For example, the local adjudication modules 216 and 226 and global adjudication module 230 are shown as separate blocks, other embodiments of the HSDP 100 can support adjudication in the data conditioning modules 210 and 220, clustering modules 212 and 222, and math processing modules 214 and 224. This distributed adjudication architecture can reduce subsequent processing to accelerate the recommendation method results.

A simplified example can demonstrate the operation and value of the HSDP 100 methods and apparatus described herein. The system processor 128 can create an entity universe for precision medicine and related investigations. The entity universe is multidimensional and can contain related feature vectors (defined by a set of attributes) such as individuals, diagnoses, diseases, and treatments (including surgical and medical procedures, drugs, etc.). Each of these entities can be selected based on one or more shared (i.e., in common) and/or not shared attributes. All attributes used in this example can span the multidimensional space of the entity universe. Information can be culled from an Electronic Medical Record (EMR) System.

Physicians can face difficult choices in managing medically complex and/or high acuity individuals. For example, individuals can have ongoing multiple disease processes and/or ongoing multiple treatments. Many different medications can be required to improve and/or maintain the individual. Some medications are given to alleviate side effects of other medications. Therefore, recommendations must consider the interaction of diseases, e.g., hypertension, diabetes, congestive heart failure, renal disease, etc., and treatments, e.g., Beta blockers, insulin, blood thinners and dialysis/transplant and immune suppressing drugs, etc. Ongoing multiple disease processes and new diseases can add uncertainty and complexity to the recommendation process.

The described embodiments can be used to decide the optimum medications and dosages that provide the best therapeutic results while minimizing side-effects for said individual. The entity universe constructed can be used 1) to discover new, existing, and/or repurposed drugs (and/or medicinal compounds) and/or a combination of these to fight the specific diseases and/or conditions, 2) to discover interactions between drugs, food, environment, and the individual's genetic make-up and/or 3) to discover unknown side-effects of combined medications.

The system processor 128 can also be used as an experimental platform for diagnosis and/or treatment. These diagnoses and treatments can include medical/pharmaceutical/biological research, etc. For example, the HSDP 100 can be used to discover new and/or modified drugs, new applications for existing drugs, and/or repurposed existing drugs or medicinal compounds, or a combination of these to fight new and/or existing disease or conditions, as well as, discover interactions between drugs, such as therapeutic and side-effects, food, environment, and genetic make-up that can be the origin of diseases and/or other conditions. The system processor 128 can create an entity universe consisting of individuals, diseases and treatments. Each entity can be represented by a feature vector composed of shared attributes. These attributes can be selected by the research and regions of the entity universe can be explored by the researcher. These attributes can include individual medical database and history, and can include genetic information. These can include individual family history, research and/or sources of genetic information, e.g., military, government, ongoing studies like Framingham Heart Study, Nurses Study, etc., and/or pharmaceutical data.

Also, the system processor 128 can identify promising regions within the entity universe for further investigation (e.g., currently incurable diseases, undiagnosed diseases, more effective therapeutic medication and/or genetic procedures. etc.) and the advent of precision medicine. A possible application of the HDSP 100 can be to determine the individuals who could be subject to a severe side effects of the Human Papilloma Virus (HPV) vaccine. This knowledge can enable the individual (or parents) and health care providers to make a more informed recommendation on administering the vaccine based on the determined recommendation(s) as described herein. The HDSP 100 can ingest the medical histories, DNA sequencing, life style, environmental factors, and medical research for a significant number of individuals, including those that had a severe side effects to the HPV vaccine. The data conditioning modules

210 and 220 can operate separately on 1) the individual medical history and environmental factors, 2) the individual's genetics, e.g., genotype, phenotype, DNA, RNA, etc., and/or 3) medical research publications. For all 3 data sources, all available information can be preprocessed to check the data consistency and/or conformance, tag data, data compression, data alignment, and any corrections, modifications, repairs and/or replacements of missing and/or out-of-bounds data. Following this process, the information can be textually processed using information theoretic (TF.IDF), syntactic, and semantic methods. The information from the individual specific source can generate intermediate vectors for 1) medical history, including treatments, family medical history, relevant research, and environmental factors and 2) DNA sequencing. The two intermediate vectors for each individual can be combined into a feature vector that represents the individual or entity. The medical research associated with HPV and related diseases can be separately textually processed into a set of "research" entities that can identify key clusters of the entity universe. Each entity can be tagged to provide a link to the original information source and/or indicate that the feature vector was limited, synthesized, or in some way altered in the data preprocessing. Dimensionality reduction in the data conditioning modules 210 and 220 can be performed on the intermediate and/or feature vectors based on a minimal acceptable loss of information. The dimensionality reduction can 1) compress/combine attributes, such as dimensions of the entity universe, 2) can weight attributes, and/or 3) eliminate regions of the entity universe containing sparse feature vectors using PCA, SVD, and/or State SVM methods. The clustering modules 212 and 222 can perform linear, nonlinear, linear manifold, and/or NLM clustering. The individual and "research" entities are then passed to the clustering modules 212 and 222 by the data conditioning data conditioning modules 210 and 220, respectively. The NLM clustering can improve differentiation of entities by using locally linear and nonlinear high-dimensional spaces that are connected via a nonlinear manifold. Following the clustering, the math model modules 214 and 224 can perform math processing that can estimate the probability distribution for each cluster and can calculate the associated statistical moments for each cluster.

The adjudication modules 216, 226, and 230 can minimize the loss function to define, as well as optimize assignment of the entities to the decision multidimensional hyper-volumes. The system can use training with supervised and/or unsupervised learning to identify the entities within decision multidimensional hyper-volumes that can have sensitivity to the HPV vaccine. The adjudication modules 216, 226, and 230 can perform iterative runs to search for environment conditions or specific DNA sequences that can increase the propensity to have a reaction to the HPV virus. The iterative runs can mask or limit large portions of the DNA and monitor the impact on the expected loss. The inputs DNA sequences, as well as environmental conditions of various interim runs that show promise can be subsequently combined to further drive the expected loss lower. The HSDP 100 can use a gradient descent method to report the findings once further iterations show marginal improvement. The expected result is a set of DNA sequences and environmental conditions that can be used to predict sensitivity to HPV vaccine side effects in individuals.

Figure 4:
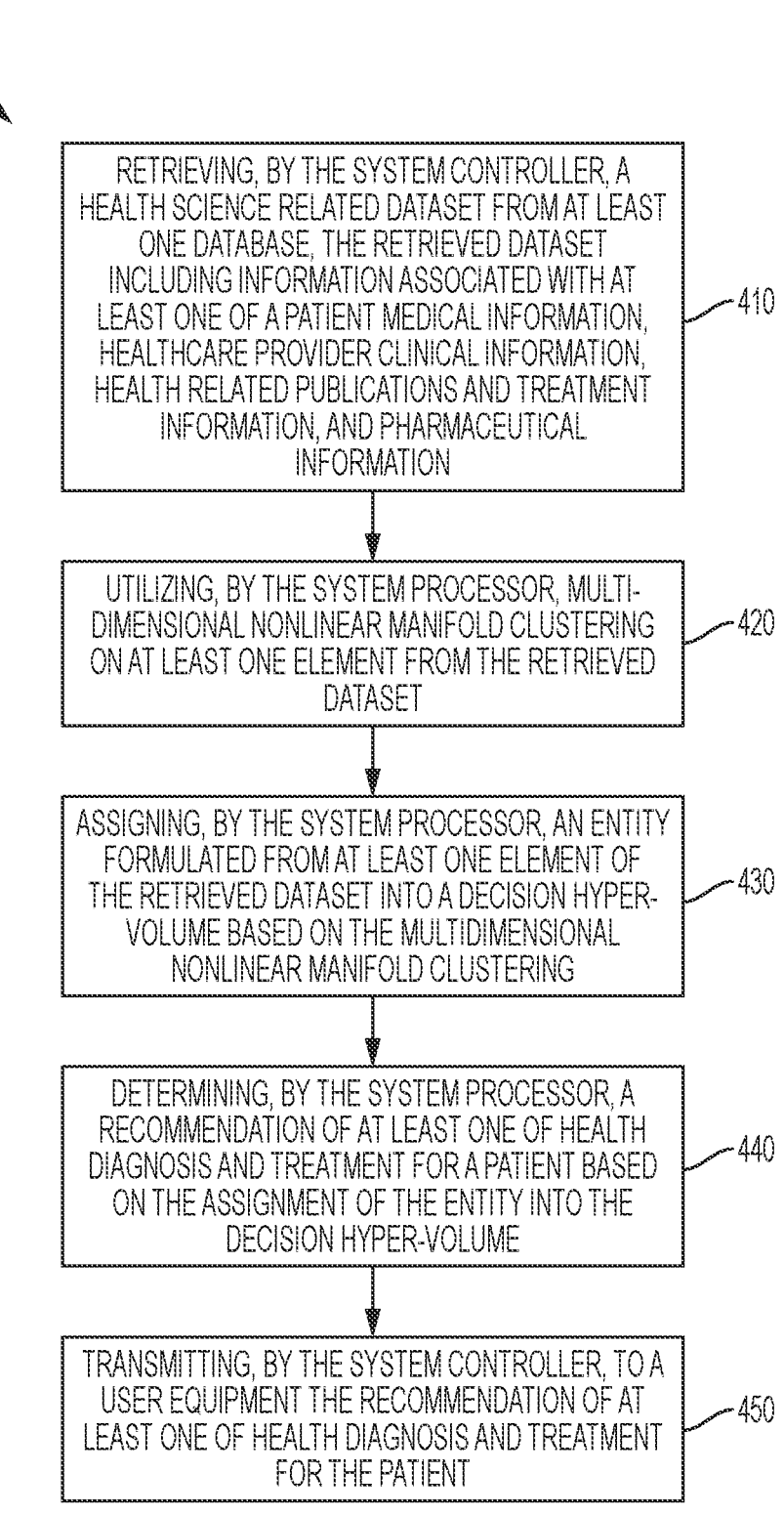
FIG. 4 illustrates an example flowchart for a method of making a recommendation for health diagnosis and/or treatment, in accordance with one or more possible embodiments.

FIG. 4 illustrates an example flowchart for a method 400 of making a recommendation for health diagnosis and/or treatment, in accordance with one or more possible embodiments. The method 400 can be performed by the HSDP 100 and/or performed, either partially or entirely, by any of the other components of the HSDP 100, as discussed above. The method 400 is not limited to the example blocks shown and can include any of the processes performed by the HSDP 100.

The method 400 of determining a recommendation of at least one of health diagnosis and treatment for a patient can begin a block 410. At block 410, a health science related retrieved dataset can be retrieved, by the system controller 126, from at least one database, the retrieved dataset including information associated with at least one of a patient medical information, healthcare provider clinical information, health related publications and treatment information, and pharmaceutical information. Block 410 proceeds to block 420.

At block 420, multidimensional nonlinear manifold clustering can be utilized, by the system processor 128, on the at least one element from the retrieved dataset. Block 420 proceeds to block 430. At block 430, an entity can be assigned, by the system processor 128, into a decision hyper-volume based on the multidimensional nonlinear manifold clustering, the entity being formulated from the at least one element of the retrieved dataset. Block 430 proceeds to block 440.

At block 440, a recommendation can be determined, by the system processor 128, of at least one of health diagnosis and treatment for the patient based on the assignment of the entity into the decision hyper-volume. Block 440 proceeds to block 450. At 450, the recommendation of at least one of health diagnosis and treatment for the patient can be transmitted, by the system controller 126, to the UE 110.

While this disclosure has been described with specific embodiments thereof, it is evident that many alternatives, modifications, and variations will be apparent to those skilled in the art. For example, various components of the embodiments may be interchanged, added, or substituted in the other embodiments. Also, all of the processing blocks of each figure may not be necessary for operation of the disclosed embodiments. For example, one of ordinary skill in the art of the disclosed embodiments would be enabled to make and use the teachings of the disclosure by simply employing the elements of the independent claims. Accordingly, embodiments of the disclosure as set forth herein are intended to be illustrative, not limiting. Various changes may be made without departing from the spirit and scope of the disclosure.

In this document, relational terms such as "first," "second," and the like may be used solely to distinguish one entity or action from another entity or action without necessarily requiring or implying any actual such relationship or order between such entities or actions. The phrase "at least one of" followed by a list is defined to mean one, some, or all, but not necessarily all of, the elements in the list. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a," "an," or the like does not, without more constraints, preclude the existence of additional identical elements in the process, method, article, or apparatus that comprises the element. Also, the term "another" is defined as at least a second or more. The terms "including," "having," and the like, as used herein, are defined as "comprising." Furthermore, the background section is written as the inventor's own understanding of the context of some embodiments at the time of filing and includes the inventor's own recognition of any problems with existing technologies and/or problems experienced in the inventor's own work.

We claim:

1. An apparatus, comprising:

a system controller to retrieve a health science related dataset from at least one database, the retrieved dataset including a plurality of attributes, each of the plurality of attributes associated with at least one of a patient medical information, healthcare provider clinical information, health related publications and treatment information, and pharmaceutical information, and transmit to a user equipment a recommendation of at least one of health diagnosis and treatment for a particular patient, wherein the user equipment is separate from the system controller; and a system processor to formulate a plurality of entities, the plurality of entities formulated based on the retrieved dataset and based on a particular patient entity formulated for the particular patient from at least one attribute of the plurality of attributes, separate, utilizing multidimensional nonlinear manifold clustering, the plurality of entities into a plurality of hyper-volumes along a nonlinear manifold, each hyper-volume including at least one entity of the plurality of entities, an entity of the at least one entity being defined by a set of the plurality of attributes defining a point in the respective hyper-volume along the nonlinear manifold, a decision hyper-volume of the plurality of hyper-volumes including a plurality of decision hyper-volume entities, the plurality of decision hyper-volume entities including the particular patient entity, and determine the recommendation of at least one of health diagnosis and treatment for the particular patient based on assignment, using the multidimensional nonlinear manifold clustering, of the particular patient entity into the decision hyper-volume.

2. The apparatus of claim 1, wherein the system processor further formulates the particular patient entity from at least one attribute of the plurality of attributes of the retrieved dataset.

3. The apparatus of claim 1, wherein the system processor further performs adjudication to minimize a loss function in order to optimize the assignment of the particular patient entity by adjusting a decision boundary of the decision hyper-volume.

4. The apparatus of claim 1, wherein the utilization of the multidimensional nonlinear manifold clustering further includes utilizing the multidimensional nonlinear manifold clustering and at least one other type of multidimensional clustering including at least one of linear clustering, linear manifold clustering, and nonlinear clustering.

5. The apparatus of claim 1, wherein the assignment of the particular patient entity into the decision hyper-volume is further based on at least one other type of multidimensional clustering including at least one of linear clustering, linear manifold clustering, and nonlinear clustering.

6. The apparatus of claim 1, wherein the system processor further performs adjudication to minimize a loss function in order to optimize the assignment of the particular patient entity by adjusting a decision boundary of the decision hyper-volume for the multidimensional nonlinear manifold clustering and at least one other type of multidimensional clustering including at least one of linear clustering, linear manifold clustering, and nonlinear clustering, and selects at least one of the multidimensional nonlinear manifold clustering and the at least one other type of multidimensional clustering based on a minimum loss function and optimum entity assignment.

7. The apparatus of claim 1, wherein the system processor further performs adjudication to control a number of iterations of selection of the retrieved dataset and compares multiple iterations of the multidimensional nonlinear manifold clustering and at least one other type of multidimensional clustering.

8. The apparatus of claim 1, wherein the system processor further utilizes a neural network to define the decision hyper-volume.

9. The apparatus of claim 1, wherein the at least one of health diagnosis includes at least one of a disease and a health condition and the treatment is at least one of surgical, radiological, pharmaceutical, deoxyribonucleic acid modification, ribonucleic acid modification, immunotherapy, environment change, and life style change.

10. The apparatus of claim 1, wherein the treatment includes at least one of discovery of a new drug, new application for an existing drug, repurpose an existing drug, drug interactions, drug side-effects, drug dosage, drug efficacy, drug sensitivity, and discovery of a complementary drug.

11. The apparatus of claim 1, wherein the at least one of health diagnosis and treatment is based on at least one of deoxyribonucleic acid, ribonucleic acid, phenotype, genotype, biomarker, exosome, environment, and life style.

12. The apparatus of claim 1, wherein the system processor further places the particular patient entity into an entity universe based on Monte Carlo insertion with or without measure of importance.

13. The apparatus of claim 1, wherein the system processor further divides the particular patient entity into two or more sub-entities.

14. The apparatus of claim 1, wherein the system processor further formulates the particular patient entity using text processing including performing at least one of Information Theoretic, semantic, and syntactic, processing, or extracting numerically encoded text features from at least one of bulk text, structured text, unstructured text, biological sequences, chemical sequences, deoxyribonucleic acid, and ribonucleic acid.

15. The apparatus of claim 1, wherein the system processor further applies the assignment of the particular patient entity regionally to an adjacent hyper-volume sharing a decision boundary.

16. The apparatus of claim 1, wherein the system processor further formulates a confidence region to rank an order of a plurality of the recommendation of the at least one of health diagnosis and treatment.

17. The apparatus of claim 1, wherein the system processor further assigns a decision of the at least one of health diagnosis and treatment to the decision hyper-volume based on at least one of supervised training and unsupervised training.

18. The apparatus of claim 1, wherein the system processor further performs adjudication to formulate at least one of the retrieved dataset and the particular patient entity, to optimize the recommendation of at least one of diagnosis and treatment.

19. The apparatus of claim 1, wherein at least one of the system processor and system controller are at least partially implemented in at least one of a local computing, distributed computing, mobile computing, cloud-based computing, Graphics Processing Unit (GPU), array processing, Field Programmable Gate Arrays (FPGA), tensor processing, Application Specific Integrated Circuits (ASIC), quantum computing, and a software program.

20. A method, comprising:

retrieving, by a system controller, a health science related dataset from at least one database, the retrieved dataset including a plurality of attributes, each of the plurality of attributes associated with at least one of a patient medical information, healthcare provider clinical information, health related publications and treatment information, and pharmaceutical information;

formulating, by a system processor, a plurality of entities, the plurality of entities formulated based on the retrieved dataset and based on a particular patient entity formulated for a particular patient from at least one attribute of the plurality of attributes;

separating, by the system processor, utilizing multidimensional nonlinear manifold clustering, the plurality of entities into a plurality of hyper-volumes along a nonlinear manifold, each hyper-volume including at least one entity of the plurality of entities, an entity of the at least one entity being defined by a set of the plurality of attributes defining a point in the respective hyper-volume along the nonlinear manifold, a decision hyper-volume of the plurality of hyper-volumes including a plurality of decision hyper-volume entities, the plurality of decision hyper-volume entities including the particular patient entity;

determining, by the system processor, a recommendation of at least one of health diagnosis and treatment for a particular patient based on assignment, using the multidimensional nonlinear manifold clustering, of the particular patient entity into the decision hyper-volume; and transmitting, by the system controller, to a user equipment the recommendation of at least one of health diagnosis and treatment for the particular patient, wherein the user equipment is separate from the system controller.

21. The method of claim 20, further comprising formulating, by the system processor, the particular patient entity from at least one attribute of the plurality of attributes of the retrieved dataset.

22. The method of claim 20, further comprising performing adjudication, by the system processor, to minimize a loss function in order to optimize the assignment of the particular patient entity by adjusting a decision boundary of the decision hyper-volume.

23. The method of claim 20, wherein the utilization of the multidimensional nonlinear manifold clustering further includes utilizing the multidimensional nonlinear manifold clustering and at least one other type of multidimensional clustering including at least one of linear clustering, linear manifold clustering, and nonlinear clustering.

24. The method of claim 20, wherein the assignment of the particular patient entity into the decision hyper-volume is further based on at least one other type of multidimensional clustering including at least one of linear clustering, linear manifold clustering, and nonlinear clustering.

25. The method of claim 20, further comprising:

performing adjudication, by the system processor, to minimize a loss function in order to optimize the assignment of the particular patient entity by adjusting a decision boundary of the decision hyper-volume for the multidimensional nonlinear manifold clustering and at least one other type of multidimensional clustering including at least one of linear clustering, linear manifold clustering, and nonlinear clustering, and selecting, by the system processor, at least one of the multidimensional nonlinear manifold clustering and the at least one other type of multidimensional clustering based on a minimum loss function and optimum entity assignment.

26. The method of claim 20, further comprising performing adjudication, by the system processor, to control a number of iterations of selection of the retrieved health science related dataset and comparing, by the system processor, multiple iterations of the multidimensional nonlinear manifold clustering and at least one other type of multidimensional clustering.

27. The method of claim 20, further comprising utilizing, by the system processor, a neural network to define the decision hyper-volume.

28. The method of claim 20, wherein the at least one of health diagnosis includes at least one of a disease and a health condition and the treatment is at least one of surgical, radiological, pharmaceutical, deoxyribonucleic acid modification, ribonucleic acid modification, immunotherapy, environment change, and life style change.

29. The method of claim 20, wherein the treatment includes at least one of discovery of a new drug, new application for an existing drug, repurpose an existing drug, drug interactions, drug side-effects, drug dosage, drug efficacy, drug sensitivity, and discovery of a complementary drug.

30. The method of claim 20, wherein the at least one of health diagnosis and treatment is based on at least one of deoxyribonucleic acid, ribonucleic acid, phenotype, genotype, biomarker, exosome, environment, and life style.

31. The method of claim 20, further comprising placing, by the system processor, the particular patient entity into an entity universe based on Monte Carlo insertion with or without measure of importance.

32. The method of claim 20, further comprising dividing, by the system processor, the particular patient entity into two or more sub-entities.

33. The method of claim 20, further comprising formulating, by the system processor, the particular patient entity using text processing including performing at least one of Information Theoretic, semantic, and syntactic, processing, or extracting numerically encoded text features from at least one of bulk text, structured text, unstructured text, biological sequences, chemical sequences, deoxyribonucleic acid, and ribonucleic acid.

34. The method of claim 20, further comprising applying, by the system processor, the assignment of the particular patient entity regionally to an adjacent hyper-volume sharing a decision boundary.

35. The method of claim 20, further comprising formulating, by the system processor, a confidence region to rank an order of a plurality of the recommendation of at least one of health diagnosis and treatment.

36. The method of claim 20, further comprising assigning, by the system processor, a decision of the at least one of health diagnosis and treatment to the decision hyper-volume based on at least one of supervised training and unsupervised training.

37. The method of claim 20, further comprising performing adjudication, by the system processor, to formulate at least one of the retrieved dataset and the particular patient entity, to optimize the recommendation of at least one of diagnosis and treatment.

38. The method of claim 20, wherein at least one of the system processor and system controller are at least partially implemented in at least one of a local computing, distributed computing, mobile computing, cloud-based computing, Graphics Processing Unit (GPU), array processing, Field Programmable Gate Arrays (FPGA), tensor processing, Application Specific Integrated Circuits (ASIC), quantum computing, and a software program.

* * * * *